United States Patent
Diep et al.

(10) Patent No.: US 11,648,289 B2
(45) Date of Patent: May 16, 2023

(54) ANTIBACTERIAL METHOD

(71) Applicant: NORWEGIAN UNIVERSITY OF LIFE SCIENCES, Aas (NO)

(72) Inventors: Dzung B. Diep, Aas (NO); Kirill V. Ovchinnikov, Aas (NO); Per E. Kristiansen, Blindern (NO); Ingolf F. Nes, Aas (NO); Tage Thorstensen, Aas (NO)

(73) Assignee: NORWEGIAN UNIVERSITY OF LIFE SCIENCES, Aas (NO)

( * ) Notice: Subject to any disclaimer, the term of this patent is extended or adjusted under 35 U.S.C. 154(b) by 0 days.

(21) Appl. No.: 17/060,648

(22) Filed: Oct. 1, 2020

(65) Prior Publication Data

US 2021/0017236 A1 Jan. 21, 2021

Related U.S. Application Data

(62) Division of application No. 16/469,757, filed as application No. PCT/EP2017/082937 on Dec. 14, 2017, now Pat. No. 10,851,139.

(30) Foreign Application Priority Data

Dec. 14, 2016 (GB) ..................................... 1621295

(51) Int. Cl.
| | | |
|---|---|---|
| *A61K 38/16* | (2006.01) | |
| *A23L 3/3571* | (2006.01) | |
| *A61L 2/16* | (2006.01) | |
| *C07K 14/195* | (2006.01) | |
| *A01N 63/50* | (2020.01) | |
| *A61K 38/00* | (2006.01) | |

(52) U.S. Cl.
CPC ............ *A61K 38/164* (2013.01); *A01N 63/50* (2020.01); *A23L 3/3571* (2013.01); *A61L 2/16* (2013.01); *C07K 14/195* (2013.01); *A23V 2002/00* (2013.01); *A61K 38/00* (2013.01); *A61L 2202/21* (2013.01); *A61L 2202/24* (2013.01)

(58) Field of Classification Search
None
See application file for complete search history.

(56) References Cited

PUBLICATIONS

Ovchinnikov et al., "The Leaderless Bacteriocin Enterocin K1 is Highly Potent against *Enterococcus faeciunr*: A Study on Structure, Target Spectrum and Receptor", Frontiers in Microbiology, 2017, vol. 8, Article 774, pp. 1-12.
Jensen, M.S., Identification of RIP metallopeptidase RseP as Target Receptor for Leaderless Bacteriocin Ej97, and the Presumptive Involvement of the Ecs ABC transporter in medium Resistance Master Thesis, Norwegian Univ. Life Sciences, Dept. Chem., Biotech. & Food Science, Dec. 2014, pp. 1-154.
Alvarez-Sieiro et al., "Bacteriocins of lactic acid bacteria: extending the family", Appl. Microbiol. Biotechnol., 2016, vol. 100, pp. 2939-2951.
Drider et al., "Bacteriocins: Not Only Antibacterial Agents", Probiotics & Antimicro Prot., 2016, vol. 8, pp. 177-182.
Miljkovic et al., "LsbB Bacteriocin Interacts with the Third Transmembrane Domain of the YvjB Receptor", Applied and Environmental Microbiology, 2016, vol. 82, No. 17, pp. 5364-5374.
Uzelac et al., "A Zn-Dependent Metallopeptidase is Responsible for Sensitivity to LsbB, a Class II Leaderless Bacteriocin of *Lactococcus lactis* subsp. lactis BGMN1-5", Journal of Bacteriology, 2013, vol. 195, No. 24, pp. 5614-5621.
Cotter et al., "Bacteriocins—a viable alternative to antibiotics?", Nature Reviews, Microbiology, 2013, vol. 11, pp. 95-105.
Ness et al., "Enterococcal Bacteriocins and Antimicrobial Proteins that Contribute to Niche Control", Enterococci, 2014, pp. 637-668.
Gajic et al., "Novel Mechanism of Bacteriocin Secretion and Immunity Carried Out by Lactococcal Multidrug Resistance Proteins", J. Biol. Chem., 2003, vol. 278, No. 36, pp. 34291-34298.
Basanta et al., "Antimicrobial activity of Enterococcus faecium L50, a strain producing enterocins L50 (L50A and L50B), P and Q, against beer-spoilage lactic acid bacteria in broth, wort (hopped and unhopped), and alcoholic and non-alcoholic lager beers", International Journal of Food Microbiology, 2008, vol. 125, pp. 293-307.
Gálvez et al., "Isolation and Characterization of enterocin EJ97, a bacteriocin produced by *Enterococcus faecalis* EJ97", Arch Microbiol, 1998, vol. 171, pp. 59-65.
Cintas, et al., "Biochemical and Genetic Evidence that *Enterococcus faecium* L50 Produces Enterocins L50A and L50B, the sec-Dependent Enterocin P, and a Novel Bacteriocin Secreted without an N-Terminal Extension Termed Enterocin Q", J. Bacteriology, 2000, vol. 182, No. 23, pp. 6806-6814.
Hyink et al., "*Streptococcus rattus* strain BHT produces both a class I two-component lantibiotic and a class II bacteriocin", FEMS Microbiology Letters, 2005, vol. 252, pp. 235-241.

(Continued)

*Primary Examiner* — Sergio Coffa
(74) *Attorney, Agent, or Firm* — Wenderoth, Lind & Ponack, L.L.P.

(57) ABSTRACT

The present invention provides a method of killing, damaging or preventing the replication of bacteria comprising administering or applying a bacteriocin to said bacteria, wherein said bacteriocin is a peptide comprising the amino acid sequence MKFKFNPTGTIVKKLTQYEIAWFKNKHGYYPWEIPRC and related sequences, wherein the bacteria is selected from *E. faecium, E. faecalis, E. hirae, S. pseudointermedius* and/or *S. hemolyticus*; and/or in said method said bacteria are subjected to a stress condition. Also provided are related methods and uses such as methods of treatment. Also provided are novel truncation and fusion proteins variants such as MIKKFPNPYTLAAKLTTYEINWYKQQYGRYPWERPVA and MKFKFNPTGTIVKKLTQYEINWYKQQYGRYPWERPVA and their use as bacteriocins in various methods and uses.

Figure 1:
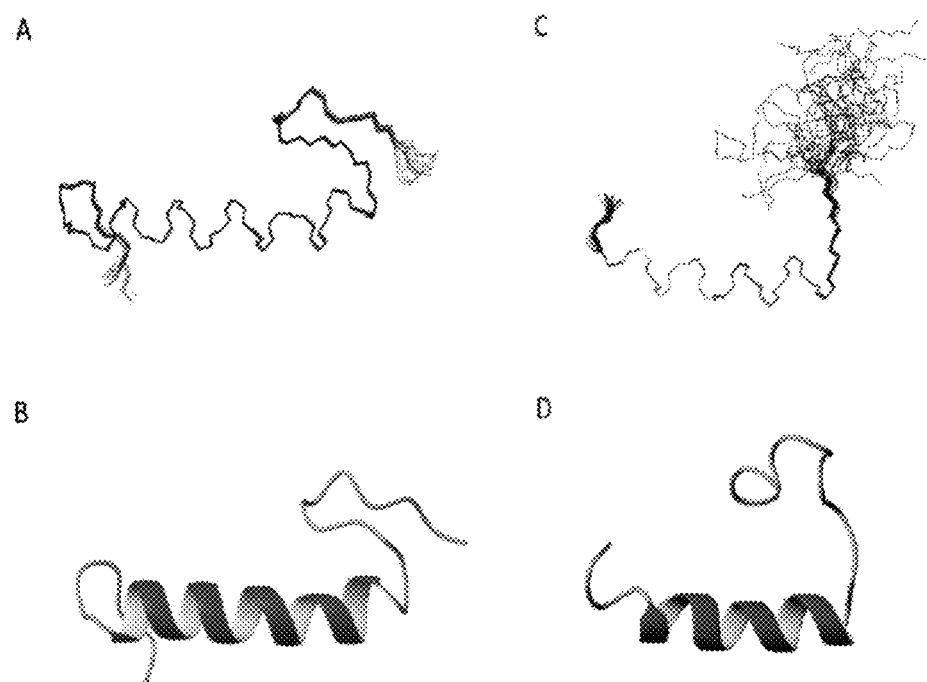

16 Claims, 2 Drawing Sheets
Specification includes a Sequence Listing.

(56) References Cited

PUBLICATIONS

Varaham et al., "An ABC Transporter is Required for Secretion of Peptide Sex Pheromones in *Enterococcus faecalis*", mBio, 2014, vol. 5, Issue 5, pp. 1-9.

Varahan et al., "Eep Confers Lysozyme Resistance to *Enterococcus faecalis* via the Activation of the Extracytoplasmic Function Sigma Factor SigV", Journal of Bacteriology, vol. 195, No. 14, pp. 3125-3134.

Alba et al, "DegS and YaeL participate sequentially in the cleavage of RseA to activate the E-dependent extracytoplasmic stress response", Genes & Development, 2002, vol. 16, pp. 2156-2168.

López et al., "Semi-preparative scale purification of enterococcal bacteriocin enterocin EJ97, and evaluation of substrates for its production", J. Ind. Microbiol. Biotechnol., 2007, vol. 34, pp. 779-785.

Viedma et al., "Effect of polythene film activated with enterocin EJ97 in combination with EDTA against Bacillus coagulans", LWT—Food Science and Technology, 2010, vol. 43, pp. 514-518.

Criado et al. "Complete Sequence of the Enterocin Q-Encoding Plasmid pCIZ2 from the Multiple Bacteriocin Producer *Enterococcus faecium* L50 and Genetic Characterization of Enterocin Q Production and Immunity", Applied Environmental Microbiology, 2006, vol. 72(10), pp. 6653-6666.

Baker et al., "Sensitization of Gram-Negative and Gram-Positive Bacteria to Jenseniin G by Sublethal Injury", Journal of Food Protection, 2004, vol. 67, No. 5, pp. 1009-1013.

Galvão et al., "Stress enhances the sensitivity of *Salmonella enterica* serovar Typhimurium to bacteriocins", Journal of Applied Microbiology, 2015, vol. 118, pp. 1137-1143.

Ovchinnikov, Kirill V., "A Study of Leaderless Bacteriocins, With Focus on Structure—Function and Receptor Characterization", Department of Chemistry, Biotechnology and Food Science, Thesis, 2016, 115 pages.

International Search Report and Written Opinion of the International Searching Authority dated Apr. 20, 2018 in International (PCT) Application No. PCT/EP2017/082937.

Ovchinnikov et al. "Defining the Structure and Receptor Binding Domain of the Leaderless Bacteriocin LsbB", J. Biol. Chem., 2014, 289(34):23838-23845.

Sanchez-Hidalgo et al. "The Genes Coding for Enterocin EJ97 Production by *Enterococcus faecalis* EJ97 are Located on a Conjugative Plasmid", Appl Environ. Microbiol., 2003, 69(3):1633-41.

SEQUENCE LISTING

<160> NUMBER OF SEQ ID NOS: 46

<210> SEQ ID NO 1
<211> LENGTH: 37
<212> TYPE: PRT
<213> ORGANISM: Enterococcus sp.

<400> SEQUENCE: 1

Met Lys Phe Lys Phe Asn Pro Thr Gly Thr Ile Val Lys Lys Leu Thr
1               5                   10                  15

Gln Tyr Glu Ile Ala Trp Phe Lys Asn Lys His Gly Tyr Tyr Pro Trp
            20                  25                  30

Glu Ile Pro Arg Cys
        35

<210> SEQ ID NO 2
<211> LENGTH: 44
<212> TYPE: PRT
<213> ORGANISM: Enterococcus sp.

<400> SEQUENCE: 2

Met Leu Ala Lys Ile Lys Ala Met Ile Lys Lys Phe Pro Asn Pro Tyr
1               5                   10                  15

Thr Leu Ala Ala Lys Leu Thr Thr Tyr Glu Ile Asn Trp Tyr Lys Gln
            20                  25                  30

Gln Tyr Gly Arg Tyr Pro Trp Glu Arg Pro Val Ala
        35                  40

<210> SEQ ID NO 3
<211> LENGTH: 37
<212> TYPE: PRT
<213> ORGANISM: Enterococcus sp.

<400> SEQUENCE: 3

Met Ile Lys Lys Phe Pro Asn Pro Tyr Thr Leu Ala Ala Lys Leu Thr
1               5                   10                  15

Thr Tyr Glu Ile Asn Trp Tyr Lys Gln Gln Tyr Gly Arg Tyr Pro Trp
            20                  25                  30

Glu Arg Pro Val Ala
        35

<210> SEQ ID NO 4
<211> LENGTH: 37
<212> TYPE: PRT
<213> ORGANISM: Artificial Sequence
<220> FEATURE:
<223> OTHER INFORMATION: EntK1J97

<400> SEQUENCE: 4

Met Lys Phe Lys Phe Asn Pro Thr Gly Thr Ile Val Lys Lys Leu Thr
1               5                   10                  15

Gln Tyr Glu Ile Asn Trp Tyr Lys Gln Gln Tyr Gly Arg Tyr Pro Trp
            20                  25                  30

Glu Arg Pro Val Ala
        35

<210> SEQ ID NO 5
<211> LENGTH: 44
<212> TYPE: PRT
<213> ORGANISM: Artificial Sequence
<220> FEATURE:
<223> OTHER INFORMATION: EJ-K1

<400> SEQUENCE: 5

Met Leu Ala Lys Ile Lys Ala Met Ile Lys Lys Phe Pro Asn Pro Tyr
1               5                   10                  15

Thr Leu Ala Ala Lys Leu Thr Thr Tyr Glu Ile Ala Trp Phe Lys Asn
            20                  25                  30

Lys His Gly Tyr Tyr Pro Trp Glu Ile Pro Arg Cys
        35                  40

<210> SEQ ID NO 6
<211> LENGTH: 22
<212> TYPE: DNA
<213> ORGANISM: Artificial Sequence
<220> FEATURE:
<223> OTHER INFORMATION: Primer Ent_F

<400> SEQUENCE: 6
cgaagtggtc aagtccaatg gt                                            22

<210> SEQ ID NO 7
<211> LENGTH: 21
<212> TYPE: DNA
<213> ORGANISM: Artificial Sequence
<220> FEATURE:
<223> OTHER INFORMATION: Primer Ent_M

<400> SEQUENCE: 7
gtgcggattg cgccacttga c                                               21

<210> SEQ ID NO 8
<211> LENGTH: 24
<212> TYPE: DNA
<213> ORGANISM: Artificial Sequence
<220> FEATURE:
<223> OTHER INFORMATION: Primer Ent_R

<400> SEQUENCE: 8
gatgacttaa gacttctgca tcat                                            24

<210> SEQ ID NO 9
<211> LENGTH: 22
<212> TYPE: DNA
<213> ORGANISM: Artificial Sequence
<220> FEATURE:
<223> OTHER INFORMATION: Primer EF_F

<400> SEQUENCE: 9
gctcttagca agatttgatg gc                                              22

<210> SEQ ID NO 10
<211> LENGTH: 22
<212> TYPE: DNA
<213> ORGANISM: Artificial Sequence
<220> FEATURE:
<223> OTHER INFORMATION: Primer EF_M

<400> SEQUENCE: 10
cgtccacact gactacctca tc                                              22

<210> SEQ ID NO 11
<211> LENGTH: 23
<212> TYPE: DNA
<213> ORGANISM: Artificial Sequence
<220> FEATURE:
<223> OTHER INFORMATION: Primer EF_R

<400> SEQUENCE: 11
cttagaccgt ttcgacagtt tgc                                             23

<210> SEQ ID NO 12
<211> LENGTH: 21
<212> TYPE: DNA
<213> ORGANISM: Artificial Sequence
<220> FEATURE:
<223> OTHER INFORMATION: Primer EF_R2

<400> SEQUENCE: 12
tgcaatctgt cgacgtgaca c                                               21

<210> SEQ ID NO 13
<211> LENGTH: 21
<212> TYPE: DNA
<213> ORGANISM: Artificial Sequence
<220> FEATURE:
<223> OTHER INFORMATION: Primer T1_F

<400> SEQUENCE: 13
agctagctca aaggaagagg c                                               21

<210> SEQ ID NO 14
<211> LENGTH: 21

```
<212> TYPE: DNA
<213> ORGANISM: Artificial Sequence
<220> FEATURE:
<223> OTHER INFORMATION: Primer T2_F

<400> SEQUENCE: 14
tgcaatctgt cgacgtgaca c                                              21

<210> SEQ ID NO 15
<211> LENGTH: 22
<212> TYPE: DNA
<213> ORGANISM: Artificial Sequence
<220> FEATURE:
<223> OTHER INFORMATION: Primer T3_F

<400> SEQUENCE: 15
gctcgaacag ctaagaatgc ct                                             22

<210> SEQ ID NO 16
<211> LENGTH: 21
<212> TYPE: DNA
<213> ORGANISM: Artificial Sequence
<220> FEATURE:
<223> OTHER INFORMATION: Primer th009

<400> SEQUENCE: 16
acgtttgagc aatttccttc c                                              21

<210> SEQ ID NO 17
<211> LENGTH: 44
<212> TYPE: DNA
<213> ORGANISM: Artificial Sequence
<220> FEATURE:
<223> OTHER INFORMATION: Primer th010

<400> SEQUENCE: 17
cacattatcc attaaaaatc aaacagcgtt tcctccgtct tttg                     44

<210> SEQ ID NO 18
<211> LENGTH: 43
<212> TYPE: DNA
<213> ORGANISM: Artificial Sequence
<220> FEATURE:
<223> OTHER INFORMATION: Primer th011

<400> SEQUENCE: 18
gtccaaaagc ataaggaaag tcgaggaata ttatgaaaca aag                      43

<210> SEQ ID NO 19
<211> LENGTH: 21
<212> TYPE: DNA
<213> ORGANISM: Artificial Sequence
<220> FEATURE:
<223> OTHER INFORMATION: Primer th012

<400> SEQUENCE: 19
catttccaac tagaagggct g                                              21

<210> SEQ ID NO 20
<211> LENGTH: 47
<212> TYPE: DNA
<213> ORGANISM: Artificial Sequence
<220> FEATURE:
<223> OTHER INFORMATION: Primer ds171

<400> SEQUENCE: 20
```

```
atttatattt attattggag gttcaatgaa aacaattatc acattca                47
```

<210> SEQ ID NO 21
<211> LENGTH: 49
<212> TYPE: DNA
<213> ORGANISM: Artificial Sequence
<220> FEATURE:
<223> OTHER INFORMATION: Primer ds172

<400> SEQUENCE: 21

```
attgggaaga gttacatatt agaaattaaa agaaaaagcg ttgaatatc              49
```

<210> SEQ ID NO 22
<211> LENGTH: 20
<212> TYPE: DNA
<213> ORGANISM: Artificial Sequence
<220> FEATURE:
<223> OTHER INFORMATION: Primer ds87

<400> SEQUENCE: 22

```
agcgtttcct ccgtcttttg                                              20
```

<210> SEQ ID NO 23
<211> LENGTH: 43
<212> TYPE: DNA
<213> ORGANISM: Artificial Sequence
<220> FEATURE:
<223> OTHER INFORMATION: Primer ds88

<400> SEQUENCE: 23

```
caaaagacgg aggaaacgct tcgaggaata ttatgaaaca aag                    43
```

<210> SEQ ID NO 24
<211> LENGTH: 24
<212> TYPE: DNA
<213> ORGANISM: Artificial Sequence
<220> FEATURE:
<223> OTHER INFORMATION: Primer Kan484.F

<400> SEQUENCE: 24

```
gtttgatttt taatggataa tgtg                                         24
```

<210> SEQ ID NO 25
<211> LENGTH: 20
<212> TYPE: DNA
<213> ORGANISM: Artificial Sequence
<220> FEATURE:
<223> OTHER INFORMATION: Primer RpsL41.R

<400> SEQUENCE: 25

```
ctttccttat gcttttggac                                              20
```

<210> SEQ ID NO 26
<211> LENGTH: 22
<212> TYPE: DNA
<213> ORGANISM: Artificial Sequence
<220> FEATURE:
<223> OTHER INFORMATION: Primer khb31

<400> SEQUENCE: 26

```
ataacaaatc cagtagcttt gg                                           22
```

<210> SEQ ID NO 27
<211> LENGTH: 25
<212> TYPE: DNA
<213> ORGANISM: Artificial Sequence -continued

```
<220> FEATURE:
<223> OTHER INFORMATION: Primer khb33

<400> SEQUENCE: 27
tttctaatat gtaactcttc ccaat                                          25

<210> SEQ ID NO 28
<211> LENGTH: 23
<212> TYPE: DNA
<213> ORGANISM: Artificial Sequence
<220> FEATURE:
<223> OTHER INFORMATION: Primer khb34

<400> SEQUENCE: 28
catcggaacc tatactcttt tag                                            23

<210> SEQ ID NO 29
<211> LENGTH: 25
<212> TYPE: DNA
<213> ORGANISM: Artificial Sequence
<220> FEATURE:
<223> OTHER INFORMATION: Primer khb36

<400> SEQUENCE: 29
tgaacctcca ataataaata taaat                                          25

<210> SEQ ID NO 30
<211> LENGTH: 44
<212> TYPE: DNA
<213> ORGANISM: Artificial Sequence
<220> FEATURE:
<223> OTHER INFORMATION: Primer 466p1

<400> SEQUENCE: 30
ggtattcttg tcctcgtagc tgaatttggc cacttttatt ttgc                     44

<210> SEQ ID NO 31
<211> LENGTH: 44
<212> TYPE: DNA
<213> ORGANISM: Artificial Sequence
<220> FEATURE:
<223> OTHER INFORMATION: Primer 467p2

<400> SEQUENCE: 31
gcaaaataaa agtggccaaa ttcagctacg aggacaagaa tacc                     44

<210> SEQ ID NO 32
<211> LENGTH: 46
<212> TYPE: DNA
<213> ORGANISM: Artificial Sequence
<220> FEATURE:
<223> OTHER INFORMATION: Primer 468p1

<400> SEQUENCE: 32
attcttgtcc tcgtacatgc atttggccac ttttatttg caaaac                    46

<210> SEQ ID NO 33
<211> LENGTH: 46
<212> TYPE: DNA
<213> ORGANISM: Artificial Sequence
<220> FEATURE:
<223> OTHER INFORMATION: Primer 469p2

<400> SEQUENCE: 33
gttttgcaaa ataaaagtgg ccaaatgcat gtacgaggac aagaat                   46
```

<210> SEQ ID NO 34
<211> LENGTH: 38
<212> TYPE: DNA
<213> ORGANISM: Artificial Sequence
<220> FEATURE:
<223> OTHER INFORMATION: Primer 470p1

<400> SEQUENCE: 34
gtacatgaat tggcgctttt ttattttgca aaacgagc        38

<210> SEQ ID NO 35
<211> LENGTH: 38
<212> TYPE: DNA
<213> ORGANISM: Artificial Sequence
<220> FEATURE:
<223> OTHER INFORMATION: Primer 471p2

<400> SEQUENCE: 35
gctcgttttg caaaataaaa agcgccaaat tcatgtac        38

<210> SEQ ID NO 36
<211> LENGTH: 32
<212> TYPE: DNA
<213> ORGANISM: Artificial Sequence
<220> FEATURE:
<223> OTHER INFORMATION: Primer 472-p1

<400> SEQUENCE: 36
gaatttggcc actttgcttt tgcaaaacga gc        32

<210> SEQ ID NO 37
<211> LENGTH: 32
<212> TYPE: DNA
<213> ORGANISM: Artificial Sequence
<220> FEATURE:
<223> OTHER INFORMATION: Primer 473-p2

<400> SEQUENCE: 37
gctcgttttg caaaagcaaa gtggccaaat tc        32

<210> SEQ ID NO 38
<211> LENGTH: 50
<212> TYPE: DNA
<213> ORGANISM: Artificial Sequence
<220> FEATURE:
<223> OTHER INFORMATION: Primer 474p1

<400> SEQUENCE: 38
attcttgtcc tcgtagctgc atttggcgcc ttttattttg caaaacgagc        50

<210> SEQ ID NO 39
<211> LENGTH: 50
<212> TYPE: DNA
<213> ORGANISM: Artificial Sequence
<220> FEATURE:
<223> OTHER INFORMATION: Primer 475p2

<400> SEQUENCE: 39
gctcgttttg caaaataaaa ggcgccaaat gcagctacga ggacaagaat        50

<210> SEQ ID NO 40
<211> LENGTH: 10
<212> TYPE: PRT
<213> ORGANISM: Artificial Sequence
<220> FEATURE:
<223> OTHER INFORMATION: Consensus sequence

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 40

Lys Xaa Xaa Xaa Gly Xaa Xaa Pro Trp Glu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Consensus sequence in EntK1

<400> SEQUENCE: 41

Lys Asn Lys His Gly Tyr Tyr Pro Trp Glu
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Consensus sequence in EntEJ97

<400> SEQUENCE: 42

Lys Gln Gln Tyr Gly Arg Tyr Pro Trp Glu
1               5                   10

<210> SEQ ID NO 43
<211> LENGTH: 34
<212> TYPE: PRT
<213> ORGANISM: Lactococcus garvieae

<400> SEQUENCE: 43

Met Gly Ala Ile Ile Lys Ala Gly Ala Lys Ile Val Gly Lys Gly Val
1               5                   10                  15

Leu Gly Gly Gly Ala Ser Trp Leu Gly Trp Asn Val Gly Glu Lys Ile
            20                  25                  30

Trp Lys

<210> SEQ ID NO 44
<211> LENGTH: 34
<212> TYPE: PRT
<213> ORGANISM: Lactococcus garvieae

<400> SEQUENCE: 44

Met Gly Ala Ile Ile Lys Ala Gly Ala Lys Ile Ile Gly Lys Gly Leu
1               5                   10                  15
```

```
Leu Gly Gly Ala Ala Gly Gly Ala Thr Tyr Gly Gly Leu Lys Lys Ile
            20                  25                  30

Phe Gly

<210> SEQ ID NO 45
<211> LENGTH: 32
<212> TYPE: PRT
<213> ORGANISM: Lactococcus garvieae

<400> SEQUENCE: 45

Met Gly Ala Ile Ile Lys Ala Gly Ala Lys Ile Val Gly Lys Gly Ala
1               5                   10                  15

Leu Thr Gly Gly Gly Val Trp Leu Ala Glu Lys Leu Phe Gly Gly Lys
            20                  25                  30

<210> SEQ ID NO 46
<211> LENGTH: 34
<212> TYPE: PRT
<213> ORGANISM: Lactococcus lactis

<400> SEQUENCE: 46

Ile Thr Ser Ile Ser Leu Cys Thr Pro Gly Cys Lys Thr Gly Ala Leu
1               5                   10                  15

Met Gly Cys Asn Met Lys Thr Ala Thr Cys Asn Cys Ser Ile His Val
            20                  25                  30

Ser Lys
```

ANTIBACTERIAL METHOD

A sequence listing in electronic (ASCII text file) format is filed with this application and incorporated herein by reference. The name of the ASCII text file is "2020-2252-Sequence Listing Revised.txt"; the file was created on Jul. 5, 2022; the size of the file is 11,237 bytes.

The present invention relates to use of a bacteriocin as defined herein as an antibacterial agent particularly when combined with the induction of a stress response. The bacteriocin is particularly useful in treating a variety of bacterial infections, particularly drug-resistant strains of bacteria. New bacteriocins are also provided.

The spread of antibiotic-resistant bacteria poses a great threat to public health and is getting worse as the current progress in developing new antibiotics is limited (Brown & Wright, 2016, Nature, 529:336-343). Aside from the introduction of carbapenems in 1985, all new antibiotics between the early 1960s and 2000 were synthetic derivatives of existing scaffolds, which often allow resistant strains to arise rapidly (Fischbach & Walsh, 2009, Science, 325:1089-1093). In the USA alone, the economic loss incurred by antibiotic resistance is estimated to be up to 55 billion USD per year with some data suggesting that the total cost may be even higher (Smith & Coast, 2013, BMJ, 346:f1493).

During the past few decades, enterococci have emerged as important healthcare-associated pathogens due to their resistance to antibiotics and environmental stress factors (Arias and Murray, 2012, Nat. Rev. Microbiol., 10:266-278). The rapid spread of *E. faecium* with resistance to vancomycin (VRE), ampicillin and high-levels of aminoglycosides is of particular concern (Agudelo Higuita and Huycke, 2014, Enterococcal Disease, Epidemiology, and Implications for Treatment. In Gilmore et al., (ed), Enterococci: From Commensals to Leading Causes of Drug Resistant Infection. Massachusetts Eye and Ear Infirmary, Boston). *E. faecium* is now a nosocomial pathogen as common as *E. faecalis* (Arias and Murray, 2012, supra).

Consequently, there is a need for new antimicrobials that can be used as alternatives to conventional antibiotics, particularly directed to *Enterococcus*.

Bacteriocins are a group of antimicrobial peptides (Cotter et al., 2013, Nat. Rev. Microbiol., 11:95-105). Bacteriocins are ribosomally synthesized peptides produced by bacteria to inhibit or kill other bacteria in competition for nutrients or habitats. They are almost without exception cationic, amphiphilic, and heat-stable. The antimicrobial inhibition spectra and potency of bacteriocins differ greatly, with the majority being active only against closely related bacteria while some having broader spectra, targeting cells from different genera (Nes et al., 2014, Enterococcal Bacteriocins and Antimicrobial Proteins that Contribute to Niche Control. In Gilmore et al. (eds), Enterococci: From Commensals to Leading Causes of Drug Resistant Infection. Massachusetts Eye and Ear Infirmary, Boston).

Bacteriocins have a number of advantages over conventional antibiotics and chemical food preservatives. Bacteriocins show antimicrobial activity at pico- to nanomolar concentrations and are common in many fermented foods and in the human gut microflora. These properties make them very attractive as natural food preservatives (Nes et al., 1996, Antonie Van Leeuwenhoek, 70:113-128). Most bacteriocins from Gram-positive bacteria are known as membrane-active peptides, i.e., they disrupt membrane integrity, leading to leakage of intracellular solutes and cell death (Kjos et al., 2011, Microbiology 157:3256-3267). This killing mechanism is different from that of most antibiotics, which often act as enzyme inhibitors of key metabolic pathways. Due to their different modes of action, bacteriocins do not discriminate between antibiotic resistant and sensitive bacteria (Nes et al., 2014, supra). However, since bacteriocin activity also causes selective pressure on bacterial populations to produce resistant strains, there remains a need for new antibacterials, particularly against drug-resistant bacteria.

The present invention has identified bacteriocins from *Enterococcus* which are effective against hard to treat bacteria, as well as methods for improving their efficacy and thus offers new strategies for killing bacteria, particularly nosocomial bacteria, particularly from *Enterococcus*, e.g. *E. faecium* and *E. faecalis*. New bacteriocins have also been identified.

Most bacteriocins undergo posttranslational modifications, including cleavage of the N-terminal leader sequence of the bacteriocin precursor by dedicated ABC transporters during exporting from the cell (Nissen-Meyer & Nes, 1997, Arch. Microbiol., 167:67-77). However, there is a group of so-called leaderless bacteriocins whose members are different from others in that they do not undergo any post-translational modifications and are synthesized without N-terminal leader sequences.

EntK1 is a member of a family of leaderless bacteriocins which presently contains four members: EntK1, LsbB, EntQ and EntEJ97 (Ovchinnikov et al., 2014, J. Biol. Chem., 289:23838-23845). LsbB is a 30 amino acid (aa) residues peptide produced by *Lactococcus lactis* and it has a very narrow inhibition spectrum which contains only lactococcal strains (Gajic et al., 2003, J. Biol. Chem., 278:34291-34298.). The remaining three bacteriocins are produced by different enterococcal strains. EntQ (34 aa residues) and especially EntEJ97 (44 aa residues) have broader antimicrobial spectra than LsbB (Basanta et al., 2008, Int. J. Food. Microbiol., 125:293-307; Galvez et al., 1998, Arch. Microbiol., 171:59-65; Cintas et al., 2000, J. Bacteriol., 182:6806-6814.). Little is known about the activity of the newly discovered EntK1 (37 aa residues), although it has been shown to inhibit *L. lactis* IL1403 (Ovchinnikov et al., 2014, J. Biol. Chem., 289:23838-23845). It has surprisingly been found that EntEJ97 and EntK1 are particularly effective in targeting *E. faecalis* and *E. faecium*, respectively. It has also been found that after treatment with these bacteriocins, mutants with high or low resistance to the bacteriocins develop. Surprisingly it has been found that these mutants are particularly sensitive to treatment with stress conditions. Variants of these molecules with different bacterial specificity (particularly for *Staphylococcus*) have also been identified.

Bacteriocins are known to bind to specific receptors on target membranes to kill cells. It has previously been shown that the site-2 protease family Zn-dependent metallopeptidase YvjB (also known as RseP) serves as LsbB receptor in *L. lactis* (Uzelac et al., 2013, J. Bacteriol., 195:5614-5621; Miljkovic et al., 2016, Appl. Environ. Microbiol., 82:5364-5374), and it is believed that the peptide binds to its receptor using its unstructured C-terminal part (Ovchinnikov et al., 2014, supra). However, the receptor for the enterococcal bacteriocins and how the enterococcal bacteriocins target genera other than *Lactococcus* was unknown. Without wishing to be bound by theory, based on the inventors' work, it is believed that the enterococcal bacteriocins bind to the RseP receptor. Mutants with high resistance to the enterococcal bacteriocins were found to have mutations in this receptor. It has also been found that these mutants (as well as low resistance mutants which do not have mutations in this receptor) are susceptible to stress factors and thus a combination of treatment with both the enterococcal bacteriocins and a stress condition provides an effective antibacterial against bacteria, even when resistant mutants might otherwise develop particularly against nosocomial *Enterococcus*.

Thus, in a first aspect the present invention provides a method of killing, damaging or preventing the replication of bacteria comprising administering or applying a bacteriocin to said bacteria, wherein said bacteriocin is a peptide comprising an amino acid sequence selected from:

a) MKFKFNPTGTIVKKLTQYEIAWFKNKHGYYPWEIPRC (SEQ ID NO:1),
b) a sequence with at least 40% sequence identity to sequence a),
c) a sequence consisting of at least 15 consecutive amino acids of sequence a), and
d) a sequence with at least 40% sequence identity to sequence c), wherein sequences b), c) and d) comprise at least the consensus sequence KXXXGXXPWE (SEQ ID NO:40), wherein X may be any amino acid, and wherein
i) said bacteria is selected from *E. faecium*, *E. faecalis*, *E. hirae*, *S. pseudointermedius* and/or *S. hemolyticus* (preferably from *E. faecium* and/or *E. faecalis*); and/or
ii) in said method said bacteria are subjected to a stress condition.

The sequences disclosed in the application are as follows:

```
SEQ ID NO: 1:
MKFKFNPTGTIVKKLTQYEIAWFKNKHGYYPWEIPRC
(EntK1)

SEQ ID NO: 2:
MLAKIKAMIKKFPNPYTLAAKLTTYEINWYKQQYGRYPWERPVA
(EntEJ97)

SEQ ID NO: 3:
MIKKFPNPYTLAAKLTTYEINWYKQQYGRYPWERPVA
(EntEJ97short).

SEQ ID NO: 4
MKFKFNPTGTIVKKLTQYEINWYKQQYGRYPWERPVA
(K1-EJ hybrid)

SEQ ID NO: 5:
MLAKIKAMIKKFPNPYTLAAKLTTYEIAWFKNKHGYYPWEIPRC
(EJ-K1 hybrid)

SEQ ID NOs: 6-39:
Primers as provided in Table 1.
```

SEQ ID NOs:40-42: bacteriocin peptide consensus sequences

SEQ ID NOs:43-46: garvicin KS and nisin bacteriocin peptide sequences.

The bacteriocins described herein have antibacterial activity. As used herein "antibacterial activity" refers to the ability of the bacteriocins to kill, damage or prevent the replication of selected bacteria under in vitro conditions, e.g. as set forth in the Examples. The bacteria are preferably as described hereinafter. (As referred to herein bacteria are referred to in both the singular and plural. In particular they are referred to in the singular when defining the type of bacteria to be targeted (i.e. the type, e.g. species, applicable to each bacterium) and in the plural when referring to the treatment to which they may be subjected (i.e. treatment of multiple microorganisms).) "Kill" refers to destruction of a bacteria to the extent that no further replication can take place. "Damage" refers to affecting the bacteria's ability to function normally, such that it may die or be unable to replicate. "Preventing replication" refers to prevention of the replication of the bacteria partially or completely, e.g. according to the percentages described hereinafter. Preferably a method, treatment or use described herein results in the death or damage of at least 25, 50, 75 or 90% of the bacteria to which the treatment is applied or prevents replication such that a bacterial infection is prevented or reduced, e.g. by at least 30, 40, 50, 60, 70, 80 or 90% relative to a control to which the treatment is not applied. In particular, the antibacterial activity is assessed by determining the MIC value against one or more bacteria. The bacteria to be tested may be selected from a strain of bacteria selected from the genera *Enterococcus*, *Listeria* and *Lactococcus* (or other bacteria as described herein). Preferably the strain is a strain as set forth in Table 3 (e.g. *E. faecium* LMGT 3104 or *E. faecalis* LMGT 3358). A bacteriocin as described herein, with antibacterial activity preferably has a MIC value of less than 500 nM, preferably less than 300 nM, especially preferably less than 100 nM, preferably against *E. faecium* LMGT 3104 or *E. faecalis* LMGT 3358. Preferably said bacteriocin has a MIC value of less than 20, 10, 5 or 2 µg/ml for a bacteria as described herein, e.g. a bacteria as set forth in Table 6A or B (of the same genera or species).

Depending on the method in which the bacteria are to be killed, damaged or their replication prevented, different methods of administration or application may be used. For example, in in vitro methods, conveniently the bacteriocin, or a composition comprising or producing the same, is directly applied to the bacteria or an object, item, cell(s) or tissue on which the bacteria is present or it is suspected it may be present. Such application may be in the form of contact with a liquid containing the bacteriocin (or composition), which may, for example, be applied via a solution or spray. Alternative preparations may also be used, which are described hereinafter. In in vivo methods, methods of administration appropriate to the bacterial infection, its site, and the animal being treated may be used, as described hereinafter. Appropriate concentrations of the bacteriocin to be used are also as described hereinafter.

A "bacteriocin" as described herein, has the sequence disclosed herein and has antibacterial activity as described hereinbefore. The bacteriocin is a peptide. As preferred to herein a "peptide" is a polymer comprising at least 15 amino acids, preferably at least 25 or 30 amino acids. Preferably the peptide contains less than 50, e.g. less than 45, 40 or 35 amino acids e.g. from 35 to 45 amino acids. In one preferred aspect the bacteriocin is not a naturally occurring molecule (e.g. its sequence may be modified or it may be made up of one or more amino acids that are not naturally occurring).

The amino acids making up the peptide may be natural L or D amino acids (preferably L amino acids). Alternatively, one or more non-naturally occurring amino acids may be present in the peptides. Such non-naturally occurring amino acids are derivatives of naturally occurring amino acids and include alkyl (e.g. methyl), nor and aminoalkyl derivatives. Appropriate derivatives are selected to maintain functionality.

The peptides for use according to the invention (or peptides of the invention) also include those which are modified without affecting the sequence of the peptide, e.g. by chemical modification, including by deglycosylation or glycosylation. Such peptides may be prepared by post-synthesis/isolation modification of the peptide without affecting functionality, e.g. certain glycosylation, methylation etc. of particular residues. The peptides for use according to the invention (or peptides of the invention) may also take the form of peptidomimetics which may be considered derivatives in which the functional features of the peptide are retained but are presented in the context of a different, e.g. non-peptide structure. Such peptidomimetics have successfully been developed and used in the art, particularly for medical applications. Peptidomimetics, particularly non-peptidic molecules may be generated through various processes, including conformational-based drug design, screening, focused library design and classical medicinal chemistry. Not only may oligomers of unnatural amino acids or other organic building blocks be used, but also carbohydrates, heterocyclic or macrocyclic compounds or any organic molecule that comprises structural elements and conformation that provides a molecular electrostatic surface that mimics the same properties of the 3-dimensional conformation of the peptide may be used and prepared by methods known in the art.

Thus the peptidomimetics may bear little or no resemblance to a peptide backbone. Peptidomimetics may comprise an entirely synthetic non-peptide form (e.g. based on a carbohydrate backbone with appropriate substituents) or may retain one or more elements of the peptide on which it is based, e.g. by derivatizing one or more amino acids or replacing one or more amino acids with alternative non-peptide components. Peptide-like templates include pseudo-peptides and cyclic peptides. Structural elements considered redundant for the function of the peptide may be minimized to retain a scaffold function only or removed where appropriate.

When peptidomimetics retain one or more peptide elements, i.e. more than one amino acid, such amino acids may be replaced with a non-standard or structural analogue thereof. Amino acids retained in the sequences may also be derivatised or modified (e.g. labelled, glycosylated or methylated) as long as the functional properties of the peptides for use according to the invention (or peptides of the invention), are retained. The peptidomimetics are referred to as being "derivable from" a certain peptide sequence. By this it is meant that the peptidomimetic is designed with reference to a defined peptide sequence, such that it retains the structural features of the peptide which are essential for its function. This may be the particular side chains of the peptide, or hydrogen bonding potential of the structure. Such features may be provided by non-peptide components or one or more of the amino acid residues or the bonds linking said amino acid residues of the peptide may be modified so as to improve certain functions of the peptide such as stability or protease resistance, while retaining the structural features of the peptide which are essential for its function.

Examples of non-standard or structural analogue amino acids which may be used are D amino acids, amide isosteres (such as N-methyl amide, retro-inverse amide, thioamide, thioester, phosphonate, ketomethylene, hydroxymethylene, fluorovinyl, (E)-vinyl, methyleneamino, methylenethio or alkane), L-N methylamino acids, D-α methylamino acids and D-N-methylamino acids.

The peptides also include derivatives which have been modified, e.g. to facilitate their use in various applications, e.g. pharmaceutical applications (discussed below), e.g. by the addition of targeting or functional groups, e.g. to improve lipophilicity, aid cellular transport, solubility and/or stability. Thus oligosaccharides, fatty acids, fatty alcohols, amino acids, peptides or polypeptides may be conjugated to the aforementioned peptides.

The peptides also encompass derivatives in the form of "pro-drugs" or "pro-peptides" such that the added component may be removed by cleavage once administered, e.g. by cleavage of a substituent added through esterification which may be removed by the action of esterases. Such pro-drugs include native precursors of the naturally occurring peptides which are cleaved e.g. by proteolysis to yield the peptide of interest. Such precursors may be inactive in the precursor form but may be activated by proteolytic cleavage.

The bacteriocin for use according to the invention is a peptide comprising an amino sequence selected from:
a) MKFKFNPTGTIVKKLTQYEIAWFKNKHGYYP-WEIPRC (SEQ ID NO:1),
b) a sequence with at least 40% sequence identity to sequence a),
c) a sequence consisting of at least 15 consecutive amino acids of sequence a), and
d) a sequence with at least 40% sequence identity to sequence c), wherein sequences b), c) and d) comprise at least the consensus sequence KXXXGXXPWE (SEQ ID NO:40), wherein X may be any amino acid.

The sequence provided above is the sequence for EntK1 (SEQ ID NO:1). Sequences with at least 40% sequence identity to a stated sequence are preferably at least 45, 55, 60, 65, 70, 75, 80, 85, 90, 95, 96, 97, 98 or 99% identical to that sequence (e.g. SEQ ID NO 1 or a 15-mer portion thereof), preferably they have at least 60, 70, 80, 90 or 95% sequence identity. Such sequences comprise the consensus sequence KXXXGXXPWE (SEQ ID NO:40). In EntK1 this sequence is KNKHGYYPWE (SEQ ID NO:41) and in EntEJ97 this sequence is KQQYGRYPWE (SEQ ID NO:42). Thus, preferably in the consensus sequence $KX_1X_2X_3GX_4X_5PWE$ (SEQ ID NO:40), $X_1$ is N or Q; $X_2$ is K or Q, $X_3$ is H or Y, $X_4$ is Y or R; and/or $X_5$ is Y. Preferably this consensus sequence appears at the C-terminus of the peptide in which it appears.

As used herein "and/or" refers to one or both of the recited options being present, e.g. A and/or B includes the options i) A, ii) B or iii) A and B. A, B and/or C includes the options i) A, ii) B, iii) C, iv) A and B; v) A and C; vi) B and C, and vii) A, B and C.

Sequence identity may be determined by, e.g. using the SWISS-PROT protein sequence databank using FASTA pep-cmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than, or equal to, 50, 40, 30, 20 or 15 contiguous amino acids. Where sequences of non-identical length are compared, the comparison is over the corresponding region which shows identity, e.g. the 40% identity in d) is established by comparison to said 15 (or more) consecutive amino acids.

Deletions, insertions and substitutions of the disclosed peptide sequences are contemplated which provide sequences with the claimed sequence identity.

As described above, the bacteriocin may comprise a sequence consisting of at least 15 consecutive amino acids of EntK1 (SEQ ID NO:1) or a sequence with at least 40% sequence identity to said sequence consisting of the at least 15 consecutive amino acids. In both cases, the sequence contains the above described consensus sequence. Preferably said sequence consists of at least 20, 25, 30 or 35 consecutive amino acids of EntK1, or a sequence with at least 40% sequence identity thereto. Consecutive amino acids are those which follow consecutively, without interruption, in the sequence as set forth. Preferably the consecutive amino acid sequences are chosen from the C-terminal end, e.g. the provided sequences (e.g. in SEQ ID NOs 1 and 2) may be truncated at the N-terminal end. Preferred values for sequence identity are as described above.

Thus, in a preferred aspect the peptide may comprise an amino acid sequence selected from:

a) a sequence consisting of at least 15 consecutive amino acids of MKFKFNPTGTIVKKLTQYEIAWFKNKHGYYPWEIPRC (SEQ ID NO:1) or MLAKIKAMIKKFPNPYTLAAKLTTYEINWYKQQYGRYPWERPVA (SEQ ID NO:2), wherein said at least 15 consecutive amino acids start at least 2, preferably 5 amino acids, from the N-terminal end, and b) a sequence with at least 50% sequence identity to sequence a), wherein sequences a) and b) comprise at least the consensus sequence KXXXGXXPWE (SEQ ID NO:40), wherein X may be any amino acid.

Thus, a truncation, may be made, preferably at the N-terminal end, of 2, 3, 4, 5, 6, 7, 8, 9, 10 or up to 15 amino acids.

In a particularly preferred feature, the peptide comprises or consists of the sequence: MIKKFPNPYTLAAKLTTYEINWYKQQYGRYPWERPVA (SEQ ID NO:3) or a sequence with at least 50% sequence identity thereto (preferably MIKKFPNPYTLAAKLTTYEINWYKQQYGRYPWERPVA, SEQ ID NO:3).

Preferred sequence identity for the above described aspects is as described hereinbefore (thus preferably, the sequence identity is at least 60, 70, 80, 90 or 95%, for example).

Furthermore, fusion (or hybrid) proteins between sequences as described herein may be made comprising at least 15 amino acids of a sequence described herein. Thus, in a further preferred aspect, the peptide comprises an amino acid sequence selected from:

a) a sequence consisting of at least 15 consecutive amino acids of MKFKFNPTGTIVKKLTQYEIAWFKNKHGYYPWEIPRC (SEQ ID NO:1) and at least 10, preferably 15, consecutive amino acids of MLAKIKAMIKKFPNPYTLAAKLTTYEINWYKQQYGRYPWERPVA (SEQ ID NO:2), and b) a sequence with at least 50% sequence identity to sequence a), wherein sequences a) and b) comprise at least the consensus sequence KXXXGXXPWE (SEQ ID NO:40), wherein X may be any amino acid.

Thus a sequence of at least 15, 16, 17, 18, 19, 20 or up to 25 or 30 consecutive amino acids of the first (listed) sequence (SEQ ID NO:1) may be used, and conjugated or fused to a sequence of at least 10, e.g. 11, 12, 13, 14, 15 or up to 20, 25 or 30 consecutive amino acids of the second sequence (SEQ ID NO:2). The first sequence may appear at the N- or C-terminal and the second sequence at the other terminal. Preferably the first sequence appears at the N-terminal. In a preferred aspect of this embodiment, said peptide comprises or consists of the sequence: MKFKFNPTGTIVKKLTQYEINWYKQQYGRYPWERPVA (SEQ ID NO:4) or a sequence with at least 50% sequence identity thereto (preferably MKFKFNPTGTIVKKLTQYEINWYKQQYGRYPWERPVA, SEQ ID NO:4). An alternative fusion peptide is provided by SEQ ID NO:5 (MLAKIKAMIKKFPNPYTLAAKLTTYEIAWFKNKHGYYPWEIPRC), MKFKFNPTGTIVKKLTQYEINWYKQQYGRYPWERPVA (SEQ ID NO:4), or a sequence with at least 50% sequence identity thereto, which also falls within the scope of the claim.

Preferred sequence identity for the above described aspects is as described hereinbefore (thus preferably, the sequence identity is at least 60, 70, 80, 90 or 95%, for example). Such variant molecules fall within the scope of embodiments described by reference to SEQ ID NO:1. In the alternative, the bacteriocin for use in the invention is a peptide as described above without reference to SEQ ID NO:1.

In a preferred aspect, the peptide comprises or consists of:

a) MKFKFNPTGTIVKKLTQYEIAWFKNKHGYYPWEIPRC (EntK1, SEQ ID NO:1) or MLAKIKAMIKKFPNPYTLAAKLTTYEINWYKQQYGRYPWERPVA (EntEJ97, SEQ ID NO:2), b) a sequence with at least 50%, preferably 90%, sequence identity to sequence a), c) a sequence consisting of at least 15 consecutive amino acids of sequence a), and d) a sequence with at least 50%, preferably 90%, sequence identity to sequence c), wherein sequences b), c) and d) comprise at least the consensus sequence KXXXGXXPWE (SEQ ID NO:40), wherein X may be any amino acid.

Preferred sequence identity for the above described aspects is as described hereinbefore (thus preferably, the sequence identity is at least 60, 70, 80, 90 or 95%, for example). Such molecules fall within the scope of embodiments described by reference to SEQ ID NO:1. In the alternative, the bacteriocin for use in the invention is a peptide as described above defined by reference to SEQ ID NO:2 without reference to SEQ ID NO:1.

EntK1 and EntEJ97 have 48% sequence identity across the 37 amino acids of EntK1. In this embodiment, said at least 90% sequence identity is at least 95, 96, 97, 98 or 99% sequence identity. (Similar preferred sequence identities are applicable to other embodiments of the invention describing 90% sequence identity.) The other features of this aspect are as described hereinbefore, including the preferred aspects. In a particularly preferred aspect, the peptide comprises or consists of the sequence: MKFKFNPTGTIVKKLTQYEIAWFKNKHGYYPWEIPRC (SEQ ID NO:1) or MLAKIKAMIKKFPNPYTLAAKLTTYEINWYKQQYGRYPWERPVA (SEQ ID NO:2), or a sequence consisting of at least 15 (or more, as described hereinbefore) consecutive amino acids thereof.

The bacteriocin which is a peptide may comprise or consist of the above described amino acid sequence. Thus, for example, the peptide may additionally contain flanking sequences, e.g. of 1-10 amino acids at the N and/or C-terminal end. These flanking sequences may be ignored in calculating sequence identity.

The peptides described herein, including the sequence identity related peptides, and peptides containing non-natural amino acids (e.g. peptidomimetics as described above) are functionally equivalent to the peptides which are set forth in the recited SEQ ID NOs 1, 2, 3 and 4 (particularly SEQ ID NOs:1 and 4). Peptides which show "functional equivalence" exhibit the same or substantially the same antibacterial effects as the peptide from which they are derived (by sequence variation or use of different amino acids). The antibacterial effects may be assessed by examining the effect of the bacteriocin on selected bacteria. Preferably a functionally equivalent peptide when tested has at least 50%, preferably at least 70, 80 or 90% of the antibacterial activity exhibited by EntK1 (and/or EntEJ97 or the described variants) on a strain of bacteria selected from the genera *Enterococcus, Listeria* and *Lactococcus* (or other bacteria on which tests have been conducted as described herein). Preferably the strain is a strain as set forth in Table 3 (e.g. *E. faecium* LMGT 3104 or *E. faecalis* LMGT 3358) or Table 6A or B. Antibacterial activity may be determined by reference to the MIC value, minimum inhibition concentration (MIC), which is defined as the minimum amount of bacteriocin that inhibits at least 50% of the growth of the bacteria in 200 μL of culture.

Particularly preferred functionally-equivalent variants are natural biological variations (e.g. allelic variants or geographical variations). In an alternative embodiment the variants may be non-natural.

The peptides described herein may be prepared by any convenient means known in the art, e.g. direct chemical synthesis or by recombinant means by expressing a nucleic acid molecule of the appropriate encoding sequence in a cell. Thus the peptides provided may be synthetic or recombinant, i.e. not produced in the bacteria in which they were identified. Alternatively the peptides may be produced from host cells as described hereinafter. The peptides for use according to the invention (or the peptides of the invention) may be isolated or purified after production.

The peptide may be provided in the form of a composition, e.g. as described hereinafter, for the uses or methods of the invention. The composition described herein may also comprise impurities, e.g. after the preparation of said composition from one of the natural sources described herein or after synthesis of the peptides. In compositions as described herein, the peptide may be present in the range of 0.001-1 mg/ml or 0.01-100 mg/ml (e.g. 0.1 to 10 mg/ml) of the composition, e.g. for use in in vitro or in vivo methods. The composition may be treated to enrich the peptide (e.g. after chemical synthesis or production in host cells) or may be used without further purification, e.g. the supernatant of the host cell expressing the peptide. Host cells expressing the peptide for use according to the invention (or the peptide of the invention) are described in more detail hereinafter.

As referred to herein, "purification" refers to removing contaminants from a sample. The peptide described herein is preferably substantially free of any contaminating components derived from the source material or materials used in the isolation procedure or in its synthetic preparation. Especially preferably the peptide is purified to a degree of purity of more than 50 or 60%, e.g. >70, 80 or 90%, preferably more than 95 or 99% purity as assessed w/w (dry weight). Such purity levels correspond to the specific molecule of interest, but includes its degradation products. Where appropriate, enriched preparations may be used which have lower purity, e.g. contain more than 1, 2, 5 or 10% of the molecule of interest, e.g. more than 20 or 30%. The peptide for use according to the invention (or peptide of the invention) may be purified by, for example, chromatography (e.g. HPLC, size-exclusion, ion-exchange, affinity, hydrophobic interaction, reverse-phase) or capillary electrophoresis.

Whilst in a preferred aspect the native sequences of EntK1 and EntEJ97 (and their variants as described herein) are used, in another aspect, non-native sequences may be used. Thus, in a preferred aspect the peptide has the features described hereinbefore but is not a peptide with the sequence as set forth in SEQ ID NOs:1 or 2.

The composition has antibacterial activity against a variety of different bacteria. Preferably the peptide has antibacterial activity against at least one (or one or more) bacteria selected from the genera *Enterococcus, Listeria* and *Lactococcus*. The peptide may also have activity against one or more strains of the genera *Staphylococcus*, e.g. *S. pseudointermedius* and/or *S. hemolyticus*. Especially preferably the composition has antibacterial activity against at least one bacteria selected from the species *Enterococcus faecalis, Enterococcus faecium, Enterococcus hirae, Listeria monocytogenes, Listeria innocua, Lactococcus garvieae, Lactococcus curvatus* and *Lactococcus cremoris*, particularly preferably Vancomycin-resistant Enterococci (VRE) (such as *E. faecalis* and/or *E. faecium*) and antibiotic-resistant strains of *Listeria monocytogenes*. The composition may also have activity against and may be used to treat *S. pseudointermedius* and/or *S. hemolyticus*. However, the invention also extends to the treatment of non-VRE *Enterococcus*. Particularly preferably said peptide has antibacterial activity against *E. faecium* and/or *E. faecalis* (particularly vancomycin-resistant strains thereof). Preferably said peptide or composition has antibacterial activity against at least one bacteria from each of the genera *Enterococcus, Listeria* and *Lactococcus*. Preferred strains against which the peptides or compositions have activity are provided in the Examples.

Thus, in a preferred aspect said bacteriocin and said bacteria are selected from:

i) said bacteriocin is a peptide comprising an amino acid sequence selected from:
   a) MKFKFNPTGTIVKKLTQYEIAWFKNKHGYYP-WEIPRC (SEQ ID NO:1),
   b) a sequence with at least 50% sequence identity to sequence a),
   c) a sequence consisting of at least 15 consecutive amino acids of sequence a), and
   d) a sequence with at least 50% sequence identity to sequence c), and said bacteria is *E. faecium, E. faecalis* or *E. hirae*, preferably *E. faecium*, preferably vancomycin-resistant *E. faecium;* ii) said bacteriocin is a peptide comprising an amino acid sequence selected from:
   a) MLAKIKAMIKKFPNPYTLAAKLT-TYEINWYKQQYGRYPWERPVA (SEQ ID NO:2),
   b) a sequence with at least 50% sequence identity to sequence a),
   c) a sequence consisting of at least 15 consecutive amino acids of sequence a), and
   d) a sequence with at least 50% sequence identity to sequence c), and said bacteria is *E. faecium, E. faecalis, E. hirae* or vancomycin-resistant *E. faecium;* iii) said bacteriocin is a peptide comprising an amino acid sequence selected from:
   a) a sequence consisting of at least 15 consecutive amino acids of MLAKIKAMIKKFPNPYTLAAKLT-TYEINWYKQQYGRYPWERPVA (SEQ ID NO:2), wherein said at least 15 consecutive amino acids start at least 2, preferably 5 amino acids, from the N-terminal end, preferably MIKKFPNPYTLAAKLT-TYEINWYKQQYGRYPWERPVA (SEQ ID NO:3), or a sequence with at least 50% sequence identity thereto, and said bacteria is *E. faecium, E. faecalis, E. hirae, S. pseudointermedius* and/or *S. hemolyticus*, preferably *E. faecalis* or *S. pseudointermedius;* and iv) said bacteriocin is a peptide comprising an amino acid sequence selected from:
   a) a sequence consisting of at least 15 consecutive amino acids of MKFKFNPTGTIVKKLTQYE-IAWFKNKHGYYPWEIPRC (SEQ ID NO:1) and at least 10, preferably 15, consecutive amino acids of MLAKIKAMIKKFPNPYTLAAKLTTYEIN WYKQQYGRYPWERPVA (SEQ ID NO:2), preferably MKFKFNPTGTIVKKLTQYEINWYKQQY GRYPWERPVA (SEQ ID NO:4), and
   b) a sequence with at least 50% sequence identity to sequence a), and said bacteria is *E. faecium, E. faecalis, E. hirae, S. pseudointermedius* and/or *S. hemolyticus*, preferably *E. faecium* or *S. haemolyticus*.

Preferably, in relation to these embodiments the sequence identity may be as described hereinbefore, for example at least 60, 70, 80, 90 or 95%. In a particularly preferred aspect the sequence identity is at least 90%. The molecules in the above embodiment fall within the scope of embodiments described by reference to SEQ ID NO:1. In the alternative, the bacteriocin for use in the invention (for treating the indicated bacteria) is a peptide as described above without reference to SEQ ID NO:1.

In the method of killing, damaging or preventing the replication of bacteria according to the invention,
i) said bacteria is selected from *E. faecium* and/or *E. faecalis* (or *E. faecium, E. faecalis, E. hirae, S. pseudointermedius* and/or *S. hemolyticus*); and/or
ii) in said method said bacteria are subjected to a stress condition.

As discussed above, peptides for use according to the invention (or the peptides of the invention) have particular use as antibacterials against *E. faecium* and/or *E. faecalis* (or *E. faecium, E. faecalis, E. hirae, S. pseudointermedius* and/or *S. hemolyticus*). In particular, peptides comprising or consisting of SEQ ID NO:1 (EntK1) or related sequences or peptides, as described herein, preferably have antibacterial activity, and may be used for this purpose, against *E. faecium*. Peptides comprising or consisting of SEQ ID NO:2 (EntEJ97) or related sequences or peptides, as described herein, preferably have antibacterial activity, and may be used for this purpose, against *E. faecalis* (and/or *E. faecium*). These molecules and their related sequences (particularly their variants as described herein) may also be used against *E. hirae, S. pseudointermedius* and/or *S. hemolyticus*.

In the alternative, or additionally, said bacteria are subjected to a stress condition during said method.

As defined herein, a "stress condition" is a condition which, when applied to living cells (either in vitro, ex vivo or in vivo) results in a cellular stress response, i.e. results in molecular changes within the cell as part of the cell's adaptive response to those conditions. Such responses are largely mediated through stress proteins. Stress conditions include heat, toxins (e.g. ethanol, metals, UV light), sugars and detergents. Preferably the stress condition is selected from heat, detergent, sugar and salt.

Whilst temperatures up to, and beyond 100° C. may be used, it has been found that effective treatment can be achieved at much lower temperatures allowing milder, but still effective, antibacterial treatments to be achieved. Conveniently, the heating may be performed from 40 to 60° C., e.g. from 45 to 55° C. or 40 to 50° C. Conveniently the heating is conducted for at least 2 hours, preferably for at least 4 hours, e.g. from 4 to 24, e.g. from 4 or 5-12 hours. The heating may be constant during this period, of may be, for example, conducted at a lower temperature for the majority of the time with one or more brief higher heating periods, e.g. during the above time periods at a temperature of around 40° C., the temperature may be raised to 50-55° C. for 10-30 minutes, one or more times.

Detergents that may be used include anionic, cationic, non-ionic and zwitterionic detergents. Sodium dodecyl sulfate (SDS) is a preferred anionic detergent. Preferred non-ionic detergents include Tween, Triton and Brij. CHAPS is a preferred zwitterionic detergent. Such detergents are preferably used at a concentration of 0.1-5% w/v for a time of 1 to 3 hours.

Sugars that may be used are sweet, water-soluble, mono- or di-saccharides. Preferred sugars are mono-saccharides such as fructose, glucose, mannose, xylose, ribose or galactose, or disaccharides such as sucrose, lactose or maltose. The monomers may be in the D or L form. Such sugars are preferably used at a concentration of 1-10% w/v for a time of 1 to 3 hours.

Salt may be any ionic compound composition of a cation and an anion. In one embodiment the cation may be a metal. Especially preferably, said salt is a potassium or sodium salt, e.g. NaCl or KCl. Preferably said salt is NaCl. Such salts are preferably used at a concentration of 5-10% w/v for a time of 3 to 24 hours.

The stress condition may be applied before, during and/or after administering or applying said bacteriocin, preferably during said administration or application. Where convenient, said stress condition which is a substance may form part of the composition containing the bacteriocin which is applied or administered during the method. Alternatively, it may be separately applied during said method, e.g. by a different route or via a different mechanism.

As discussed hereinbefore, the bacteriocin may be provided by a host cell which produces said bacteriocin. To achieve this one may use native cells which express the bacteriocin of interest and/or cells containing a nucleic acid molecule encoding a bacteriocin described herein (which may have been transformed or transfected with a nucleic acid molecule and/or recombinant construct as described hereinafter).

To provide such a host cell, nucleic acid molecules which encode the peptides described herein may be used, i.e. a nucleic acid molecule comprising a nucleotide sequence encoding a peptide as described herein.

As defined herein a nucleic acid molecule may be single or double stranded DNA, cDNA or RNA, preferably DNA. Ideally however the molecules are DNA or cDNA. Functionally equivalent molecules may also be provided, e.g. in which non-native bases are used.

Whilst native molecules may be used, in one embodiment non-native nucleic acid molecules are provided, e.g. which contain at least one, two or three nucleotide modifications (e.g. addition, deletion or substitution) relative to the native sequence.

The polynucleotides described herein may be provided as free molecules (e.g. providing just the encoding or RNA sequence), or may be provided in a recombinant construct, e.g. operatively linked with regulatory, control, marker or other sequences of interest, to allow intracellular expression of the peptides for use according to the invention (or the peptides of the invention), as a gene product, the expression of which is directed by the gene(s) introduced into cells of interest. Such a recombinant nucleic acid molecule comprises a regulatory sequence, and at least one nucleotide sequence as defined herein.

A "recombinant nucleic acid molecule" as referred to herein is a non-native nucleic acid molecule. The molecule contains a regulatory sequence which is not a regulatory sequence found in conjunction with the encoding sequences to which it is attached, i.e. the encoding sequences are heterologous relative to the regulatory sequence. Where appropriate the recombinant nucleic acid molecule may be in the form of an expression cassette to allow expression. Appropriate expression vectors include appropriate control sequences such as for example translational (e.g. start and stop codons, ribosomal binding sites) and transcriptional control elements (e.g. promoter-operator regions, termination stop sequences) linked in matching reading frame with the nucleic acid molecules as described herein. Appropriate promoters may be used to allow low, high or inducible expression. Appropriate vectors may include plasmids and viruses (including both bacteriophage and eukaryotic viruses). Thus, the nucleic acid molecules, e.g. in the form of recombinant constructs, may be presented in a vector molecule, e.g. in a plasmid. Suitable viral vectors include baculovirus and also adenovirus, adeno-associated virus, herpes and vaccinia/pox viruses. Many other viral vectors are described in the art. Preferred vectors include bacterial and mammalian expression vectors pGEX-KG, pEF-neo and pEF-HA. One or more constructs, vector molecules and/or plasmids may be used for the nucleic acid molecules as described in more detail hereinafter.

To allow expression, conveniently a recombinant nucleic acid molecule, e.g. in the form of a vector or plasmid, may be used for incorporation in the genome or for independent replication or transient transfection/expression in a cell. Conveniently integration into the genome is achieved, e.g. by homologous recombinant technology. Suitable transformation or transfection techniques are well described in the literature and may be used to introduce such vectors into prokaryotic or eukaryotic cells for expression. Alternatively, the naked nucleic acid molecule (e.g. DNA molecule) may be introduced directly into the cell for the uses described herein.

Nucleic acid molecules may be introduced into a host cell by any appropriate means. Suitable transformation or transfection techniques are well described in the literature. A variety of techniques are known and may be used to introduce such vectors into prokaryotic or eukaryotic cells for expression. Preferred host cells for this purpose include insect cells, plant cells, eukaryotic cells and prokaryotic cells. Preferably the host cell is a microorganism. Preferred microorganisms are bacteria, such as lactic acid bacteria (e.g. *Lactobacillus* or *Lactococcus*) or *E. coli*. Yeasts may also be used.

Thus the bacteriocin may be provided in a host cell selected from:
 a) a host cell producing the bacteriocin (peptide) as defined herein with the proviso that said peptide is not a native product of said host cell; and
 b) a host cell containing a nucleic acid molecule encoding the bacteriocin (peptide) as defined herein (including recombinant nucleic acid molecules described herein) (e.g. in a recombinant construct as defined herein). Preferred host cells according to a) are host cells which comprise a recombinant nucleic acid molecule as described herein. When the host cell contains a nucleic acid molecule as described herein (including a recombinant nucleic acid molecule as described herein), the nucleic acid sequence on said construct may be native (or not native) to said host cell. In one embodiment the peptides may be overexpressed in their natural/native host cells. In a particularly preferred embodiment, the host cell (which may or may not be native) produces the SEQ ID NO:1 or 2 (or SEQ ID NO:3 or 4) peptide (or sequence related peptide) as described herein.

The peptide bacteriocin for use according to the invention (or of the invention) may be prepared from a host cell as described herein by growing (e.g. culturing) said host cell under conditions whereby said peptide is expressed and recovering said peptide thus produced. The peptides may be purified, e.g. as described hereinbefore.

The bacteriocin peptides described herein may be co-administered or co-applied with one or more additional antibacterial agent. Antibacterial agents in this context refer to agents which are able to kill one or more bacteria though not necessarily with the same potency as the bacteriocins for use according to the invention (or bacteriocins of the invention). Appropriate agents include additional bacteriocins or antibiotics. Preferred antibiotics include penicillins (such as penicillin and amoxicillin), cephalosporins (such as cephalexin (Keflex)), macrolides (such as erythromycin (E-Mycin), clarithromycin (Biaxin) and azithromycin (Zithromax)), fluoroquinolones (such as ofloxacin (Cipro), levofloxacin (Levaquin) and ofloxacin (Floxin)), sulfonamides (such as co-trimoxazole (Bactrim) and trimethoprim (Proloprim)), tetracyclines (such as tetracycline (Sumycin, Panmycin) and doxycycline (Vibramycin)) and aminoglycosides (such as gentamicin (Garamycin) and tobramycin (Tobrex)). Preferred bacteriocins include nisin, pediocin PA-1, BHT-B (Hyink et al., 2005, FEMS Microbiol. Lett., 252:235-241) and garvicin ML. In addition more than one (e.g. two or three) of the peptide bacteriocins for use according to the invention (or of the invention) may be used in the composition, e.g. a co-mixture of EntK1 and EntEJ97 (or their related sequences or peptides as defined herein).

Conveniently when one or more additional antibacterial agent is used, the bacteriocin and the antibacterial agent may be provided in a composition. Alternatively they may be in separate solutions or compositions allowing different mechanisms or timings for administration or application. As referred to herein "co-administration" and "co-application" refers to use of both components in the same method rather than simultaneous use (either in terms of timing or in the same composition).

As described hereinbefore, the methods may be used in vitro, ex vivo or in vivo. In a preferred embodiment, in such methods a stress condition is used. In in vitro methods, in particular, essentially any of the above stress conditions described hereinbefore may be used. Preferred in vitro methods are to preserve food products, to avoid food spoilage and to disinfect or decontaminate an item.

Thus the antibacterial effect of the bacteriocins described herein may be used to preserve food products to prevent their spoilage. Thus, in a further aspect, the present invention provides a method of preparing a preserved food product comprising adding a bacteriocin as defined herein to a food product and optionally subjecting said food product to a stress condition as defined hereinbefore (in relation to both the type of stress condition and how it would be employed in said method).

A "preserved" food product refers to a food product to which a bacteriocin described herein (which may be in the form of a composition or a host cell, as described herein) has been applied to provide antibacterial (preservative) properties. A "food product" is an edible product that may be consumed by animals which provides nutritional benefits. Food products include in particular animal-derived food products, such as dairy and meat products as well as plant-derived food products. Various foods and beverages which may be susceptible to bacterial infection are contemplated. When host cells are to be added, these may be in the form of, for example, a plant or plant part containing those host cells and that plant, plant part or an extract thereof may be added to the food product, e.g. as an addition to a beverage which may also provide nutritional benefits, e.g. in sports drinks.

The invention thus further provides a preserved food product comprising a food product and a peptide, composition or a host cell (preferably microorganism) as defined herein.

The invention also provides a method of avoiding food spoilage comprising mixing a food product with a bacteriocin as defined herein (which may be in the form of a composition or a host cell, as described herein) and optionally subjecting said food product to a stress condition as described hereinbefore.

Food "spoilage" refers to a reduction in the nutritional properties, decay or bacterial infection of food. The food is mixed with the bacteriocin in appropriate proportions to provide beneficial antibacterial properties but without substantial deleterious effects on the taste or nutritional properties of the food product. Appropriate concentrations may be readily determined by methods known in the art.

The bacteriocin (e.g. provided in compositions and host cells) as described herein may also be used to provide antibacterial properties to non-food items, e.g. medical products. Thus, in a further aspect the present invention provides a method of disinfecting or decontaminating an item, of bacteria present on said item, comprising covering, impregnating, or coating said item with a bacteriocin or applying said bacteriocin to said item, wherein said bacteriocin is as defined herein, wherein
i) said bacteria is selected from *E. faecium* and/or *E. faecalis* (or *E. faecium, E. faecalis, E. hirae, S. pseudointermedius* and/or *S. hemolyticus*); and/or
ii) in said method said bacteria are subjected to a stress condition as defined hereinbefore.

As used herein "disinfecting" or "decontaminating" refers to killing, damaging or preventing the replication of bacteria (as defined herein), to the extent that at most 5%, e.g. at most 1% (preferably 0%) of bacteria remain (or bacteria with the ability to replicate remain) after the treatment relative to the amount of bacteria present at the start of the treatment.

The "item" refers to any inanimate object. Preferably the item is a medical device, instrument, implement or equipment, a prosthetic or material, tissue or wound dressing. Medical devices include pacemakers and heart valves, medical implements include catheters and scalpels, medical equipment includes gloves and other clothing, prosthetics or material include artificial joints, breast implants and scaffold material. Wound dressings include plasters and bandages as well as cements, glues or matrices which may be used for wound repair.

The item may also be a personal health care product (including cosmetic products). The product may be a product which is susceptible to bacterial contamination or which may be used to provide antibacterial protection to the body to which it is applied. Thus, the health care products may be body, face or lip milks, foams, sprays, lotions, creams, gels or balms, make-up products (such as eye or face products, including eye shadow, powder, lipstick, foundation, mascara, blush, eyeliner, nail polish, tinted creams and foundations, sun make-up), creams, lotions or colourants, hair products such as hair rinse, spray mist, gel, mousse, shampoo, conditioner, lotion, emulsion or colouring product and oral health or dental products such as toothpaste, mouthwash, mouth gel or spray, lozenge or chewing gum. Preferably the product is toothpaste, mouthwash, skin cream, lotion or spray.

The item or product is covered, impregnated, coated or mixed with the bacteriocin (e.g. in the form of a composition or provided by host cells) in appropriate proportions to provide beneficial antibacterial properties but without substantial deleterious effects on the item or product, e.g. its functional properties. Appropriate concentrations and methods of covering, impregnation or coating may be readily determined by methods known in the art.

In such methods of disinfecting or decontaminating, i) the bacteria is selected from *E. faecium* and/or *E. faecalis* (or *E. faecium, E. faecalis, E. hirae, S. pseudointermedius* and/or *S. hemolyticus*); and/or ii) the bacteria are subjected to a stress condition as defined hereinbefore. Preferably both a bacteriocin and a stress condition are used against the bacteria and the bacteria is preferably as described herein. The stress condition is as defined hereinbefore and may be used on said item as described hereinbefore (e.g. at the concentrations and timings described hereinbefore).

The use of a bacteriocin as described herein to prepare such items or products is also considered an object of the invention.

The bacteriocins described herein may be used as antibacterials in in vitro, ex vivo or in vivo methods. Thus, a further aspect of the invention provides use of a bacteriocin as defined herein as an antibacterial, wherein
i) said bacteriocin is used as an antibacterial against *E. faecium* and/or *E. faecalis* (or *E. faecium, E. faecalis, E. hirae, S. pseudointermedius* and/or *S. hemolyticus*); and/or
ii) said bacteriocin is used together with a stress condition as defined hereinbefore.

In a preferred aspect said bacteriocin and stress condition are used against a bacteria as defined herein (e.g. the bacteriocin may be provided in a composition or by a host cell, e.g. a microorganism). The stress condition is as defined hereinbefore and may be used in said use as described hereinbefore (e.g. at the concentrations and timings described hereinbefore).

As described hereinafter, the bacteriocin for use in the invention (or bacteriocin of the invention) has particular utility in various therapeutic and prophylactic methods and uses. The bacteriocin may be used as a peptide, and optionally may be provided in a composition or host cell. When used, the host cells may be in a more complex structure which may be used to prepare a composition or may be used directly for the claimed methods and uses. For example, if the host cell is a plant cell, plant material comprising the host cells may be generated and the plant material used for preparing compositions or used directly for the methods and uses of the invention.

To achieve the methods and uses of the invention (including the in vitro and ex vivo methods described herein) the active ingredients, i.e. the peptide or the host cell, may be appropriately modified for use in a pharmaceutical or probiotic composition or a composition for use in preparing food products or other items or products. For example the peptide or host cell used in accordance with the invention (or peptide or host cell of the invention) may be stabilized against degradation for example by the use of appropriate additives such as salts or non-electrolytes, acetate, SDS, EDTA, citrate or acetate buffers, mannitol, glycine, HSA or polysorbate.

Thus, the peptide or host cell may be provided in the form of a pharmaceutical composition comprising in addition one or more pharmaceutically acceptable diluents, carriers or excipients, which may be for use, e.g. in therapy as described herein. Similar diluents, carriers or excipients may also be provided in compositions for non-pharmaceutical compositions but are not necessarily of pharmaceutical grade, e.g. for antibacterial protection of products. "Pharmaceutically acceptable" as referred to herein refers to ingredients that are compatible with other ingredients of the composition or host cells (or products) as well as physiologically acceptable to the recipient.

Conveniently, for in vivo methods or uses, the host cell or peptides may be provided as part of a probiotic composition. As referred to herein a "probiotic" is a live microorganism (a yeast or bacteria) that renders health benefits to the host when consumed in adequate quantities. For example, they may help in enhancing the microbial gut flora of the host and prevent proliferation of death-causing diseases. They may also help in reducing instances of gastrointestinal problems, enhance immunity of the consumer and improve skin and gut functionality. The host cell defined herein may be a probiotic, e.g. a lactic acid bacteria and thus provide a probiotic for uses as described herein. However, in a preferred aspect, the compositions comprising the bacteriocin described herein and for use according to the invention (or of the invention) may additionally comprise a probiotic microorganism which provides additional health benefits. In order to provide health benefits both the host cell and the probiotic microorganism are preferably live (as is preferred in other compositions described herein), and remain capable of replication in the patient/subject after administration.

Thus, compositions for use in the invention (or according to the invention) include a probiotic composition comprising a composition or host cell (preferably microorganism) as defined herein, wherein said composition additionally comprises at least one probiotic microorganism (which is not a host cell (microorganism) as described herein). In a preferred aspect the probiotic microorganism is a lactic acid bacteria, preferably selected from the genus *Lactobacillus* or *Streptococcus*, preferably *Lactobacillus bulgaricus, Lactobacillus bifidus* and *Streptococcus thermophilus*.

The compositions described herein (e.g. containing a bacteriocin peptide as described herein) may be formulated in a conventional manner with one or more physiologically acceptable (where necessary) carriers, excipients and/or diluents, according to techniques well known in the art using readily available ingredients. Thus, the active ingredient may be incorporated, optionally together with other active substances as a combined preparation, with one or more conventional carriers, diluents and/or excipients, to produce conventional galenic preparations such as tablets, pills, powders (for topical administration or inhalation), lozenges, sachets, cachets, elixirs, suspensions (as injection or infusion fluids), emulsions, solutions, syrups, sprays, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, aglinates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents or for nasal delivery, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrant, polymer, propellant, alkalinizing or acidifying agent, opacifier, colouring agents and fatty compounds and the like.

The compositions described herein may be formulated so as to provide quick, sustained or delayed release of the active ingredient after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

These particles may carry appropriate surface molecules to improve circulation time (e.g. serum components, surfactants, polyoxamine908, PEG etc.).

The use of solutions, sprays, suspensions, gels and emulsions are preferred, e.g. the active ingredient may be carried in water, a gas, a water-based liquid, an oil, a gel, an emulsion, an oil-in water or water-in-oil emulsion, a dispersion or a mixture thereof.

Compositions may be for topical (i.e. to the skin or mucosal membranes), oral or parenteral administration, e.g. by injection. Injections may be used to provide systemic effects or to provide local effects at the site of infection.

Topical compositions and administration are however preferred, and include gels, creams, ointments, sprays, lotions, liniments, salves, sticks, soaps, powders, films, aerosols, drops, foams, solutions, emulsions, suspensions, dispersions e.g. non-ionic vesicle dispersions, milks and any other conventional pharmaceutical or cosmetic forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

Alternatively, the compositions may be provided in a form adapted for oral or parenteral administration. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

In view of the antibacterial properties of the peptides, compositions and host cells described herein they may be used for therapeutic or prophylactic purposes. In particular, the peptide, composition or host cell (preferably microorganism) as defined herein may be used for therapy. In particular the peptides, compositions and host cells may be used in treating or preventing bacterial infection. The peptides, compositions and host cells may be suitable for treating humans or for veterinary use.

Thus, in a further aspect the present invention provides a bacteriocin (which may be in the form of a composition or provided by a host cell, as described herein) for use in treating or preventing a bacterial infection in a subject or patient, wherein said treating or preventing is to comprise administering said bacteriocin to said subject or patient or a part of said subject's or patient's body, wherein said bacteriocin is as defined herein, wherein
i) said bacteria is selected from *E. faecium* and/or *E. faecalis* (or *E. faecium, E. faecalis, E. hirae, S. pseudointermedius* and/or *S. hemolyticus*); and/or
ii) in said treating or preventing said subject or patient or a part of said subject's or patient's body is subjected to a physiologically acceptable stress condition as defined hereinbefore.

Alternatively expressed, the invention provides use of a bacteriocin (which may be in the form of a composition or provided by a host cell, as described herein) in the preparation of a medicament for treating or preventing a bacterial infection in a subject or patient, wherein said treating or preventing is to comprise administering said bacteriocin to said subject or patient or a part of said subject's or patient's body, wherein said bacteriocin is as defined herein, wherein
i) said bacteria is selected from *E. faecium* and/or *E. faecalis* (or *E. faecium, E. faecalis, E. hirae, S. pseudointermedius* and/or *S. hemolyticus*); and/or
ii) in said treating or preventing said subject or patient or a part of said subject's or patient's body is subjected to a physiologically acceptable stress condition as defined hereinbefore.

In an alternative aspect the present invention provides a method of treating or preventing a bacterial infection in a subject or patient, comprising administering a bacteriocin (which may be in the form of a composition or provided by a host cell, as described herein) to said subject or patient or a part of said subject's or patient's body, wherein said bacteriocin is as defined herein, wherein
i) said bacteria is selected from *E. faecium* and/or *E. faecalis* (or *E. faecium, E. faecalis, E. hirae, S. pseudointermedius* and/or *S. hemolyticus*); and/or
ii) in said treating or preventing said subject or patient or a part of said subject's or patient's body is subjected to a physiologically acceptable stress condition as defined hereinbefore.

Preferably in these aspects of the invention said bacteriocin and stress condition are used against a bacteria as defined herein.

Said stress condition is essentially as described hereinbefore, subject to the requirement that it is a physiologically acceptable stress condition. In this context a "physiologically acceptable" stress condition is one that is compatible with the continued health of the subject or patient, i.e. does not cause temporary or permanent damage to cells of the individual. As such, stress conditions must be selected which are compatible with in vivo systems. Thus, if heating is selected, it must be as close to physiological levels as possible and localized to the area of infection. Where the stress condition is achieved by the addition of a stress molecule, e.g. a detergent, salt or sugar, the molecule to be used and its concentration must be appropriately selected. To minimize the impact on the subject or patient, local administration of the stress condition should be performed, e.g. in a locally applied medicament. The stress condition is applied to at least the part of the patient's or subject's body which has said bacterial infection or which is susceptible to said infection.

Furthermore, the present invention also provides a product containing a peptide as described herein and optionally one or more additional active ingredients (e.g. an additional antibacterial as described hereinbefore) as a combined preparation for simultaneous, separate or sequential use in human or animal therapy, preferably as described herein.

As defined herein "treatment" (or treating) refers to reducing, alleviating or eliminating one or more symptoms of the bacterial infection which is being treated, relative to the symptoms prior to treatment. Such symptoms may be correlated with the abundance of bacteria present on the treated patient or subject. "Prevention" (or preventing or prophylaxis) refers to delaying or preventing the onset of the symptoms of the bacterial infection. Prevention may be absolute (such that no bacterial infection occurs) or may be effective only in some individuals or for a limited amount of time.

As referred to herein a "bacterial infection" is invasion of bodily tissue by a bacteria that proliferates at that site and which may result in injury to that tissue. Preferably the bacterial infection is a skin infection (preferably caused by *Enterococcus* or *Listeria*, or by *S. pseudointermedius* and/or *S. hemolyticus*).

Preferably the bacterial infection is caused by at least one bacteria as described herein, e.g. selected from the genera *Enterococcus*, *Listeria* and *Lactococcus* (or *Staphylococcus*), preferably selected from the species *Enterococcus faecalis, Enterococcus faecium, Enterococcus hirae, Listeria monocytogenes, Listeria innocua* and *Lactococcus garvieae* (and/or *S. pseudointermedius* and/or *S. hemolyticus*). In a particularly preferred aspect the bacterial infection is caused by Vancomycin-resistant Entercocci (VRE) (e.g. vancomycin resistant *E. faecium* and/or *E. faecalis*) and antibiotic-resistant strains of *Listeria monocytogenes*. However, the invention also extends to the treatment of non-VRE *Enterococcus*.

Animals (or patients/subjects) to which the peptides, compositions or host cells may be applied or administered include mammals, reptiles, birds, insects and fish particularly during fish aquaculture (e.g. salmon or cod). Preferably the animals to which the peptides, compositions or host cells are applied are mammals, particularly primates, domestic animals, livestock and laboratory animals. Thus preferred animals include mice, rats, rabbits, guinea pigs, cats, dogs, monkeys, pigs, cows, goats, sheep and horses. Especially preferably the compositions are applied, or administered, to humans. A "part" of the subject or patient refers to a body part of area to be treated, e.g. an infected region of the skin or other organ of the body.

The administration may be by any suitable method known in the medicinal arts, including for example oral, parenteral (e.g. intramuscular, subcutaneous, intraperitoneal or intravenous), intestinal, percutaneous, buccal, rectal or topical administration or administration by inhalation. The preferred administration forms will be administered orally (e.g. in food for animals), or most preferably topically. As will be appreciated oral administration has its limitations if the active ingredient is digestible. To overcome such problems, ingredients may be stabilized as mentioned previously. In a particularly preferred aspect the bacterial infection is an infection on the skin and/or the bacteriocin/composition/host cell is administered topically.

It will be appreciated that since the active ingredient for performance of the invention takes a variety of forms, e.g.

a host cell (which may itself be contained in a more complex structure) or peptides, the form of the composition and route of delivery will vary. Preferably however liquid solutions, creams or suspensions would be employed, particularly e.g. for oral delivery or topical administration. In instances in which the host cell is provided in a more complex structure which itself may be ingested, the host cells may be ingested directly, e.g. plant material, or in a product prepared therefrom, e.g. an extract which may be solid or liquid.

The concentration of active ingredient in solution or compositions containing or providing the peptide bacteriocin described herein, depends upon the nature of the compound used (i.e. the peptides or host cells), the mode of administration, the course of treatment, the age and weight of the patient/subject, the medical indication, the body or body area to be treated and may be varied or adjusted according to choice. Generally however, appropriate concentration ranges for the peptide of the composition (whether applied directly or assessed based on the production levels expected in vivo from host cells expressing the peptide) described herein are 0.0001, 0.0005, 0.001 or 0.01 to 25%, e.g. 0.0005-15%, e.g. 0.01 to 10%, such as 0.1 or 0.5 to 5, e.g. 1-5% (w/w of the final preparation for administration, particularly for topical administration). Said concentrations are determined by reference to the amount of the peptide itself and thus appropriate allowances should be made to take into account the purity of the composition. Effective single doses for a bacteriocin peptide as described herein may lie in the range of from 0.1-100 mg/cm$^2$/day, preferably 0.1-10 mg/cm$^2$/day, when applied topically, depending on the animal being treated, taken as a single dose.

The present invention also provides novel variants of the bacteriocins as described herein. Unexpectedly and as disclosed in the Examples these variants have superior antibacterial properties against particular bacteria. In particular truncated variants and fusion peptides of the disclosed bacteriocins are provided.

Thus, a further aspect of the invention provides a bacteriocin peptide comprising an amino acid sequence selected from:
a) a sequence consisting of at least 15 consecutive amino acids of MLAKIKAMIKKFPNPYTLAAKLT-TYEINWYKQQYGRYPWERPVA (SEQ ID NO:2), wherein said at least 15 consecutive amino acids start at least 2, preferably 5 amino acids, from the N-terminal end, preferably MIKKFPNPYTLAAKLT-TYEINWYKQQYGRYPWERPVA (SEQ ID NO:3), or a sequence with at least 50% sequence identity thereto, and
b) a sequence consisting of at least 15 consecutive amino acids of MKFKFNPTGTIVKKLTQYE-IAWFKNKHGYYPWEIPRC (SEQ ID NO:1) and at least 10, preferably 15, consecutive amino acids of MLAKIKA-MIKKFPNPYTLAAKLTTYEINWYKQQYGRYPWER-PVA (SEQ ID NO:2), preferably MKFKFNPTG-TIVKKLTQYEINWYKQQYGRYPWERPVA (SEQ ID NO:4), or a sequence with at least 50% sequence identity thereto.

In a particularly preferred aspect the present invention provides a bacteriocin peptide comprising an amino acid sequence selected from:
a) MIKKFPNPYTLAAKLTTYEINWYKQQYGRYPWER-PVA (SEQ ID NO:3), or a sequence with at least 50% sequence identity thereto, and
b) MKFKFNPTGTIVKKLTQYEINWYKQQYGRYPW-ERPVA (SEQ ID NO:4), or a sequence with at least 50% sequence identity thereto.

The definitions and considerations provided hereinbefore in relation to previously described bacteriocins apply also to these bacteriocins. In particular the number of truncations, consecutive amino acids, sequence identity, methods of production, variants, presence or absence of flanking sequences and so forth are as described hereinbefore. In a particularly preferred feature in relation to these embodiments the sequence identity may be, for example, at least 60, 70, 80, 90 or 95%. In a particularly preferred aspect the sequence identity is at least 90%.

The invention also extends to a composition comprising the bacteriocin peptide (or a host cell containing the same) as described herein. This may be in the form of a pharmaceutical composition comprising in addition one or more pharmaceutically acceptable diluents, carriers or excipients, which may be for use, e.g. in therapy as described herein. The invention also provides a product containing the bacteriocin peptide as described herein and optionally one or more additional active ingredients (e.g. an additional antibacterial as described hereinbefore) as a combined preparation for simultaneous, separate or sequential use in human or animal therapy, preferably as described herein.

The invention also provides a nucleic acid molecule comprising a nucleotide sequence encoding a peptide as described hereinbefore. The nucleic acid molecule is as defined hereinbefore. The polynucleotide may be provided as a free molecule or may be provided in a recombinant construct as described hereinbefore. Such a recombinant nucleic acid molecule comprises a regulatory sequence, and at least one nucleotide sequence as defined hereinbefore. The bacteriocin may also be provided in a host cell, as described hereinbefore. Thus the invention also provides a recombinant nucleic acid molecule comprising a regulatory sequence, and at least one nucleotide sequence as defined hereinbefore. The recombinant nucleic acid molecule may be as described hereinbefore, and may be a plasmid or vector, for example. The invention further provides a host cell comprising a nucleic acid molecule or recombinant nucleic acid molecule as described hereinbefore. The host cell may be used to prepare the bacteriocin and thus further provided is a method of preparing a bacteriocin as described hereinbefore comprising growing (e.g. culturing) said host cell under conditions whereby said peptide is expressed and recovering said peptide thus produced. The peptides may be purified, e.g. as described hereinbefore.

The bacteriocin according to the invention may be used as described for the other bacteriocins described hereinbefore. Thus they may be used to treat or kill particular bacteria (e.g. *E. faecium, E. faecalis, E. hirae, S. pseudointermedius* and/or *S. hemolyticus*). Conveniently they may be used in methods described herein, but not limited to such methods. In particular they may be used in all of the methods or uses as described hereinbefore, but are not limited to the specific bacteria to which the methods or uses should be applied or to the use of stress conditions. By way of example, the present invention also provides a method of killing, damaging or preventing the replication of bacteria comprising administering or applying a bacteriocin as defined herein to said bacteria. In a further embodiment use of a bacteriocin as defined herein as an antibacterial is also provided. Furthermore, a method of treating or preventing a bacterial infection in a subject or patient comprising administering a bacteriocin as defined herein to said subject or patient or a part of said subject's or patient's body is provided herein. Similarly, methods of preparing preserved food products, avoiding food spillage, disinfecting or decontaminating an item, for use in treating or preventing a bacterial infection or use in the preparation of a medicament for treating or preventing a bacterial infection in a subject or patient are also provided in which the methods and uses (and their preferred aspects) are as described herein, but are not limited to specific bacteria or the use of stress conditions.

The methods described in the Examples form further preferred aspects of the invention. All combinations of the preferred features described above are contemplated, particularly as described in the Examples. The invention will now be described by way of non-limiting Examples with reference to the drawings in which:

FIG. 1 shows the NMR structure of EntK1 (A, B) compared with LsbB (C, D) (Ovchinnikov et al., 2014, J. Biol. Chem., 289:23838-23845) in 50% TFE. The structures ensembles of the 20 lowest energy structures superimposed are shown in A and C and cartoon representations of the lowest energy structures are shown in B and D.

Figure 2:
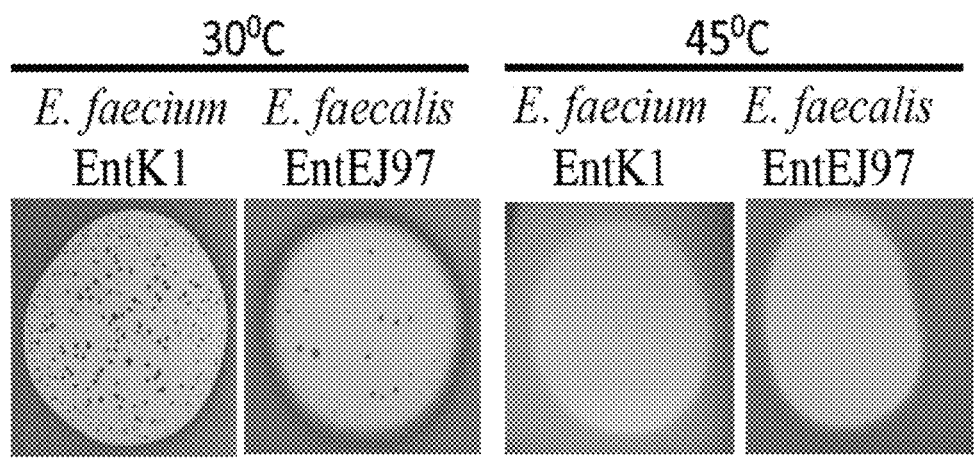

FIG. 2 shows the effect of heating on the development of EntK1 and EntEJ97 resistant mutants. Bacteriocin (20 µl of 1 mg/ml) was applied to soft agar containing indicator cells on plates, which was then incubated overnight at indicated temperatures for growth and developing the inhibition zones and resistant colonies. The mutants still appear after culture at 30° C. but not at the elevated temperature of 45° C.

EXAMPLES

Example 1: Structural Analysis of EntK1, Analysis of Inhibitory Spectra of Bacteriocins, Analysis of Resistant Mutants and Effect of Stress Conditions on Mutants Materials and Methods Bacterial strains, growth conditions, bacteriocins and antimicrobial assays. All the strains (see below) used in minimal inhibitory concentration (MIC) assays (Varahan et al., 2014, M. Bio. 5:e01726-01714) were grown in BHI medium (Oxoid) at 30° C. without shaking. A collection of *E. faecium* strains isolated from blood in patients from different European hospitals was received from Department of Medical Microbiology, University Medical Center Utrecht, the Netherlands. LsbB, EntK1, EntEJ97 and BHT-B were synthesized by Pepmic Co., LTD, China with 98-99% purity. Synthesized peptides were solubilized to concentrations of 10.0-0.1 mg/ml in 0.1% (vol/vol) trifluoroacetic acid and stored at −20° C. until use. Garvicin ML was purified to 95% as described by (Borrero et al., 2011, Appl. Environ. Microbiol., 77:369-373). Bacteriocin activity was determined by microtiter plate assay as previously described (Holo et al., 1991, J. Bacteriol., 173:3879-3887). The MIC was defined as the minimal bacteriocin concentration that inhibited the growth of the indicator strain by at least 50% (50% of the turbidity of the control culture without bacteriocin) in 200 µl culture.

CD Spectroscopy

Circular dichroism (CD) spectra were recorded using a Jasco J-810 spectropolarimeter (Jasco International Co) calibrated with D-camphor-10-sulfonate (Icatayama Chemical). All measurements were made using a quartz cuvette (Sterna) with 0.1 cm path length. Samples were scanned five times with a scanning rate of 50 nm/min with a bandwidth of 0.5 nm and response time of 1 s over the wavelength range 190-250 nm. Spectra were recorded at different (30 and 50%) trifluoroethanol (TFE) (Aldridge) concentrations at 25° C. The approximate α-helical content of the protein was estimated from its molar ellipticity at 222 nm (Scholtz et al., 1991, Biopolymers 31:1463-1470).

NMR Spectroscopy

The experiments were run on a sample containing 1.0 mM EntK1, 50% D3-TFE (99.5% D) (Aldrich), Milli-Q water and 0.2 mM of 4,4-dimethyl-4-silapentane-1-sulfonic acid (DSS) (Larodan).

2D NOESY (Jeener et al., 1979, J. Magn. Reson., 71:4546-4553), 2D TOCSY (Braunschweiler and Ernst, 1983, J. Magn. Reson., 53:521-528), 2D DQCOSY, $^{15}$N-HSQC (Davis et al., 1992, J. Magn. Reson., 98:207-216) and $^{13}$C-HSQC (Hurd, 1991, J. Magn. Reson., 91:648-653) were recorded. The data was acquired on a 600 MHz Bruker Avance II spectrometer with four channels and a 5 mm TCI cryoprobe (Bruker Biospin). NOESY spectra with mixing times between 120 ms and 300 ms were obtained for both samples. TOCSY mixing times of 15-80 ms were used. The experiments were run at 298.15 K. Spectra were processed using the Topspin program (Bruker Biospin). 4,4-dimethyl-4-silapentane-1-sulfonic acid (DSS) was used as a chemical shift standard, and $^{15}$N and $^{13}$C data were referenced using frequency ratios as described in (Wishart et al., 1995, J. Biomol. NMR., 6:135-140).

For visualization, assignment and integration of the spectra the computer program CARA was used (Keller, 2004, The Computer Aided Resonance Assignment Tutorial. CANTINA Verlag, Goldau, Switzerland). The spectra were assigned using standard methods.

Dihedral angle restraints were obtained from the chemical shift values using the program TALOS-N(Shen and Bax, 2013, J. Biomol. NMR, 56:227-241). Nuclear Overhauser effect (NOE) distance restraints were calculated from the peak volumes in the NOESY spectra with NOESY mixing time of 200 ms.

All structure calculations were made using the structure calculation program CYANA 2.1 (Guntert et al., 1997, J. Mol. Biol., 273:283-298; Herrmann et al., 2002, J. Mol. Biol., 319:209-227). The annealing macro in CYANA calculated 100 structures. The 20 structures with the lowest energy were kept and analyzed further. The root-mean-square deviation (RMSD) was calculated and the structures were visualized using MolMol (Koradi et al., 1996, J. Mol. Graph., 14:51-55, 29-32).

Generation of bacteriocin resistant mutants of *E. faecalis* and *E. faecium*. EntEJ97 and EntK1 resistant mutants were obtained by a spot-on-lawn assay using 20 µl of bacteriocin with concentrations of 1.0-0.1 mg/ml. After overnight incubation at 30° C., resistant colonies of *E. faecalis* LMGT3358 (resistant to EntEJ97) and *E. faecium* LMGT2787 (resistant to EntEJ97 and EntK1) were picked randomly from the BHI agar plates. The level of resistance against EntEJ97 and EntK1 was determined by a microtitre plate assay (Holo et al., 1991, supra). DNA from the bacteriocin resistant mutants was extracted from overnight cultures with a GenElute™ Bacterial Genomic DNA Kit (Sigma-Aldrich) and PCR of the rseP gene was performed using primers Ent, EF (F, M, R) (Table 1). For sequencing of *E. faecium* LMGT2787 mutants with transposons inside rseP, additional primers (EF_R2, T1_F, T2_F and T3_F) were created (Table 1). PCR products were purified with NucleoSpin Extract II (Macherey-Nagel, Duren, Germany) and sent to GATC Biotech, Germany, for sequencing.

Construction of *S. pneumoniae* transformants and mutants of rseP.

To express the *E. faecalis* rseP gene heterologously in *S. pneumoniae*, the gene was placed by homologous recombination in the genome of strain SPH131, behind the ComS-inducible $P_{comX}$ promoter (ComRS system) (Berg et al., 2011, J. Bacteriol., 193:5207-5215). The $P_{comX}$-rseP construct was created by overlap extension PCR (Higuchi et al., 1988, Nature. 332:543-546). First, the *E. faecalis* LMGT3358 rseP was amplified using the primer pair ds171/ds172 with genomic *E. faecalis* DNA as template. The $P_{comX}$ promoter and its ~1000 bp upstream and downstream regions were amplified using the primer pairs khb31/khb36 and khb33/khb34, respectively. Genomic DNA derived from strain SPH131 served as template. The $P_{comX}$ with its upstream region was fused to the 5' end of the *E. faecalis* rseP gene using the primers khb31 and ds172. The $P_{comX}$ downstream fragment was fused to the 3' end of the rseP gene using primer pair ds171 and khb34. Finally, these two fragments were fused using primer khb31 and khb34 giving rise to $P_{comX}$-rseP. The Janus cassette (Sung et al., 2001, Appl. Environ. Microbiol., 67:5190-5196) in strain SPH131 was replaced with the $P_{comX}$-rseP fragment by natural transformation, giving rise to strain ds218.

*S. pneumoniae* has a gene homologous to the lactococcal rseP. To avoid the potential background noise of the *S. pneumoniae* rseP, this gene was removed from the genome in strain ds218 using the Janus cassette (Sung et al., 2011, supra). An rseP deletion cassette was constructed by amplifying Janus with the primers kan484F and RpsL41.R (Johnsborg et al., 2008, Mol. Microbiol. 69:245-253) where genomic DNA from strain RH426 (Johnsborg et al., 2008, supra) served as template. The Janus cassette was then fused to the ~1000 bp upstream (primers th009 and th010 with genomic RH1 (Johnsborg et al., 2008, supra) DNA as template) and downstream region (primers th011 and th012 with genomic RH1 DNA as template) of rseP using primers th009 and th012. The resulting fragment was used to transform strain ds218 resulting in the replacement of *S. pneumoniae* rseP with Janus generating strain ds219. Janus was then removed from strain ds219 by transforming with a fragment consisting of the rseP flanking regions only. This fragment was constructed by amplifying the rseP ~1000 bp upstream region using primers th009 and ds87, while the ~1000 bp downstream region was amplified with the primers ds88 and th012. The upstream and downstream fragments were then fused using the primers pair th009/th012. The resulting fragment was used to replace the Janus in strain ds219 resulting in strain ds220.

To create a strain expressing point mutated rseP genes we replaced the *E. faecalis* 3358 rseP in strain ds220 with Janus cassette giving rise to strain ds221. This Janus cassette was amplified with the primer pair khb31/khb34 and genomic DNA from strain SPH131 served as template. Selected residues in RseP were substituted with alanines by a PCR approach, using primer pairs listed in Table 1. The resulting DNA pair fragments were subsequently fused using the primers khb31 and khb34. The resulting fragment was used to replace Janus cassette in strain ds221 giving rise to strains ms1-5 (Table 2). Ectopic expression of the rseP gene in strain ds220 and ms1-5 was induced with the synthetic ComS peptide (NH2-LPYFAGCL-COOH) (Genosphere Biotechnologies) as described by Berg et al. (2011, supra).

Results

Structural analysis of EntK1 by CD and NMR-spectroscopy. CD spectra of EntK1 showed that it was unstructured in water but became structured in TFE solution (data not shown). Maximum structuring was obtained in 50% TFE (55% α-helical content). This concentration was consequently used in the NMR experiment.

The NMR spectra were assigned using standard methods as described in Materials and Methods. Chemical shift indexing indicates that there is an α-helix in EntK1 from residue 8 to 27 and TALOS-N torsion angle predictions (Shen & Bax, 2013, supra) indicated backbone torsion angles (ϕ- and Ψ-angle) consistent with α-helical regions from residue 8 to 25 (data not shown).

A total of 561 (15.1 per residue) unique NOE connectivities were assigned (data not shown). In the presence of TFE, the observed connectivities indicated an α-helical region stretching from residue 8 to 26.

Structures of EntK1 based on the experimentally obtained constrains were calculated using CYANA. A superimposition of the structure ensemble of the 20 lowest energy structures of EntK1 and the cartoon depiction of the lowest energy structure of EntK1 are shown in FIGS. 1A and B respectively. The NMR structure of EntK1 contains an α-helix from residue 8 to residue 24. The structure ensemble has been deposited to the Protein Data Bank with access code: 5L82 and the NMR data have been deposited to the Biomagnetic Resonance Data Bank with the access code 34006.

The inhibitory spectra of EntK1 and two homologous bacteriocins.

A sizable collection of Gram-positive bacteria from different species and genera was used as indicators to assess the inhibition spectra of the bacteriocins EntK1, EntEJ97 and LsbB (Table 3, 4). EntQ, which is a member of the LsbB family bacteriocins, was not tested because synthetic EntQ peptides had poor activity, likely due to formation of disulphide bridges between and inside the molecules and was only active when mixed with reducing agents (DTT, 2-mercaptoethanol). As seen in Table 3, the antimicrobial spectra of EntK1, LsbB, and EntEJ97 differ greatly. LsbB was only active against *L. lactis* IL1403. EntK1 was active mostly against *E. faecium* and *E. hirae* and some lactococcal strains. EntEJ97 showed the broadest activity spectrum, inhibiting *E. faecium*, *E. faecalis*, *L. lactis*, *S. aureus*, *L. garvieae*, and *L. monocytogenes*. It is important to note that EntK1 appeared to have significantly lower MIC values (i.e., being more potent) than EntEJ97 against *E. faecium* (Table 3). Similarly, all three bacteriocins were active against *L. lactis* IL1403, but LsbB was about 340 and 70 times more potent than EntK1 and EntEJ97, respectively (Table 3). Since EntK1 and EntEJ97 were active against *E. faecium*, we wanted to test these two bacteriocins against *E. faecium* strains isolated from blood in patients from different European hospitals, including VRE strains. The results showed that both bacteriocins could inhibit the nosocomial strains with EntK1 being more active that EntEJ97 as in the case of non-nosocomial isolates (Table 4).

Susceptible *E. faecalis* and *E. faecium* can be adapted to provide resistant mutants in response to EntEJ97 and EntK1. The strains *E. faecalis* LMGT3358 and *E. faecium* LMGT2787 were exposed to various concentrations of EntEJ97 and EntK1 at 30° C. and many resistant colonies appeared within the inhibition zones on agar plates (see below). For *E. faecalis*, twelve EntEJ97 resistant colonies were randomly selected and examined for resistance to EntEJ97 by microtiter assays. For *E. faecium* the same was done for six EntEJ97 and six EntK1 mutants.

Two levels of *E. faecalis* resistance to EntEJ97 were found: seven colonies were highly resistant (HR)—at least 500 times more compared to the WT. The second set of five colonies showed a lower resistance (LR) level, being 16-32 times more resistant than the WT *E. faecalis*. For *E. faecium* only HR (500 times) type mutants were found. When all these mutants were challenged with the non-related bacteriocins BHT-B (Hyink et al., 2005, FEMS Microbiol. Lett., 252:235-241) and garvicin ML (Borrero et al., 2011, supra), the mutants were found as sensitive as the WT strains (data not shown). These results clearly imply the involvement of specific resistance mechanism(s) toward EntEJ97/EntK1 amongst these mutants.

Highly resistant mutants of E. faecalis and E. faecium have mutations in the rseP gene.

We investigated whether the Enterococcus homologue of the lactococcal RseP (receptor for LsbB), might serve the same function for the EntEJ97/EntK1 bacteriocins. The DNA regions containing rseP in all the EntEJ97/EntK1-resistant mutants (high and low) were therefore obtained by PCR and sequenced. All HR mutants contained a mutation within the rseP gene. The E. faecalis, resistant mutants contained either one or three consecutive 8-bp CAAAAAAT sequence repeats in the rseP gene, while the WT rseP has two such repeats. All the E. faecium HR mutants carried a transposon within the rseP gene (data not shown). In all cases, mutations caused frameshift in the rseP gene and premature termination, indicating that a functional ResP is necessary for the sensitivity toward EntEJ97/EntK1. Surprisingly, no mutations were found in rseP from all EntEJ97 LR mutants, indicating that additional genes can affect the sensitivity of the bacterium to these bacteriocins.

RseP expression in S. pneumoniae confers sensitivity to EntEJ97/EntK1.

In order to confirm that the expression of rseP is sufficient to confer sensitivity to EntEJ97 and EntK1, the rseP gene from E. faecalis LMGT3358 was inserted into the genome of the distantly related and non-sensitive host S. pneumoniae strain SPH131 as described in (Berg et al., 2011, supra). The endogenous rseP of S. pneumoniae SPH131 was removed to avoid potential background noise. In the final construct of S. pneumoniae ds220 (lacking the endogenous rseP) enterococcal rseP expression was under the control of the inducible promoter $P_{comX}$ (Berg et al., 2011, supra). While non-induced cells were not sensitive to EntEJ97 and EntK1, they became sensitive to the bacteriocins upon induction of rseP (Table 5). The results indicate that the enterococcal rseP is indeed directly involved in the sensitivity to EntEJ97 and EntK1.

The active site of RseP is partly involved in the sensitivity to the EntEJ97/EntK1 bacteriocins.

Members of the RseP protein family have a conserved proteolytic motif (HExxH, where x is any amino acid) located within the first transmembrane helix (Koide et al., 2007, J. Biol. Chem., 282:4553-4560). To analyze whether this active site is important for bacteriocin sensitivity, we changed the invariant residues in this motif —H18-E19-F20-G21-H22—one by one and altogether in the enterococcal RseP (invariant residues underlined) to alanine and then assessed for bacteriocin sensitivity. In addition, Y24 was replaced with alanine to serve as a control. The result showed that all strains expressing an RseP protein in which conserved residues were changed to alanines became more resistant to EntEJ97 and EntK1, especially when all three conserved residues were replaced with alanines (30 times more resistant to EntEJ97 than the WT) (Table 5). When a residue outside the active center was replaced with alanine (Y24>A) no changes in the bacteriocin sensitivity were observed. This result demonstrates that the active site of RseP is essential for bacteriocin activity. However, since none of the mutants became completely resistant to EntEJ97, there must be one or more additional sites in RseP involved in bacteriocin interaction.

EntK1 and EntEJ97 resistant mutants become sensitive at elevated growth temperature.

We examined how elevated growth temperature, which is a stress factor, influences the development of EntEJ97 and EntK1 resistance in E. faecium and E. faecalis. Resistant mutants only appeared at 30° C. but not at 45° C. (FIG. 2). Cell counts of cultures grown for 8 hours at 30° C. and 45° C. in BHI broth showed that the cell number at 30° C. was only about 1.2 times higher than that at 45° C. (data not shown), implying that the lack of resistant mutants at the elevated temperature was not due to poor growth. The EntEJ97/EntK1 resistant mutants with a non-functional rseP gene (described above) obtained at 30° C. could not grow at 45° C., while WT cells grew well (data not shown).

TABLE 1

Primers used in the experiments.

| Primer | Oligonucleotide sequence (5' → 3') (SEQ ID NO) | Reference |
|---|---|---|
| Ent_F | CGAAGTGGTCAAGTCCAATGGT (SEQ ID NO: 6) | This study |
| Ent_M | GTGCGGATTGCGCCACTTGAC (SEQ ID NO: 7) | This study |
| Ent_R | GATGACTTAAGACTTCTGCATCAT (SEQ ID NO: 8) | This study |
| EF_F | GCTCTTAGCAAGATTTGATGGC (SEQ ID NO: 9) | This study |
| EF_M | CGTCCACACTGACTACCTCATC (SEQ ID NO: 10) | This study |
| EF_R | CTTAGACCGTTTCGACAGTTTGC (SEQ ID NO: 11) | This study |
| EF_R2 | TGCAATCTGTCGACGTGACAC (SEQ ID NO: 12) | This study |
| T1_F | AGCTAGCTCAAAGGAAGAGGC (SEQ ID NO: 13) | This study |
| T2_F | TGCAATCTGTCGACGTGACAC (SEQ ID NO: 14) | This study |
| T3_F | GCTCGAACAGCTAAGAATGCCT (SEQ ID NO: 15) | This study |
| th009 | ACGTTTGAGCAATTTCCTTCC (SEQ ID NO: 16) | This study |
| th010 | CACATTATCCATTAAAAATCAAACAGCGTTTCCTCCGTCTTTTG (SEQ ID NO: 17) | This study |

TABLE 1-continued

Primers used in the experiments.

| Primer | Oligonucleotide sequence (5' → 3') (SEQ ID NO) | Reference |
|---|---|---|
| th011 | GTCCAAAAGCATAAGGAAAGTCGAGGAATATTATGAAACAAAG (SEQ ID NO: 18) | This study |
| th012 | CATTTCCAACTAGAAGGGCTG (SEQ ID NO: 19) | This study |
| ds171 | ATTTATATTTATTATTGGAGGTTCAATGAAAACAATTATCACATTCA (SEQ ID NO: 20) | This study |
| ds172 | ATTGGGAAGAGTTACATATTAGAAATTAAAAGAAAAAGCGTTGAATATC (SEQ ID NO: 21) | This study |
| ds87 | AGCGTTTCCTCCGTCTTTTG (SEQ ID NO: 22) | This study |
| ds88 | CAAAAGACGGAGGAAACGCTTCGAGGAATATTATGAAACAAAG (SEQ ID NO: 23) | This study |
| Kan484.F | GTTTGATTTTTAATGGATAATGTG (SEQ ID NO: 24) | (Johnsborg et al 2008) |
| RpsL41.R | CTTTCCTTATGCTTTTGGAC (SEQ ID NO: 25) | (Johnsborg et al 2008) |
| khb31 | ATAACAAATCCAGTAGCTTGG (SEQ ID NO: 26) | (Berg et al 2011) |
| khb33 | TTTCTAATATGTAACTCTTCCCAAT (SEQ ID NO: 27) | (Berg et al 2011) |
| khb34 | CATCGGAACCTATACTCTTTTAG (SEQ ID NO: 28) | (Berg et al 2011) |
| khb36 | TGAACCTCCAATAATAAATATAAAT (SEQ ID NO: 29) | (Berg et al 2011) |
| 466p1 | GGTATTCTTGTCCTCGTAGCTGAATTTGGCCACTTTTATTTTGC (SEQ ID NO: 30) | This study |
| 467p2 | GCAAAATAAAAGTGGCCAAATTCAGCTACGAGGACAAGAATACC (SEQ ID NO: 31) | This study |
| 468p1 | ATTCTTGTCCTCGTACATGCATTTGGCCACTTTTATTTTGCAAAAC (SEQ ID NO: 32) | This study |
| 469p2 | GTTTTGCAAAATAAAAGTGGCCAAATGCATGTACGAGGACAAGAAT (SEQ ID NO: 33) | This study |
| 470p1 | GTACATGAATTTGGCGCTTTTTATTTTGCAAAACGAGC (SEQ ID NO: 34) | This study |
| 471p2 | GCTCGTTTTGCAAAATAAAAAGCGCCAAATTCATGTAC (SEQ ID NO: 35) | This study |
| 472-p1 | GAATTTGGCCACTTTGCTTTTGCAAAACGAGC (SEQ ID NO: 36) | This study |
| 473-p2 | GCTCGTTTTGCAAAAGCAAAGTGGCCAAATTC (SEQ ID NO: 37) | This study |
| 474p1 | ATTCTTGTCCTCGTAGCTGCATTTGGCGCCTTTTATTTTGCAAAACGAGC (SEQ ID NO: 38) | This study |
| 475p2 | GCTCGTTTTGCAAAATAAAAGGCGCCAAATGCAGCTACGAGGACAAGAAT (SEQ ID NO: 39) | This study |

(Johnsborg et al., 2008, Mol. Microbiol. 69: 245-253; Berg et al., 2011, J. Bacteriol., 193: 5207-5215)

TABLE 2

S. pneumoniae strains used in the experiments.

| Strain | Genotype/relevant features[a] | Reference/source |
|---|---|---|
| RH1 | S. pneumoniae, R704, but ebg::spc; Ery[r] Spc[r] | Johnsborg et al., 2008 |
| RH426 | S. pneumoniae, contains the Janus cassette; Ery[r] Kan[r] | Johnsborg et al., 2008 |
| SPH131 | S. pneumoniae, contains the ComRS system, Janus cassette is placed behind $P_{comX}$; Ery[r] Kan[r] | Berg et al., 2011 |
| ds218 | S. pneumoniae SPH131 but Δjanus::rseP from E. faecalis LMGT5833 | This study |
| ds219 | S. pneumoniae ds218 but ΔrseP$_{wt}$::janus | This study |
| ds220 | S. pneumoniae ds219 but Δjanus | This study |
| ds221 | S. pneumoniae ds220 but Δ rseP::janus | This study |
| ms1 | S. pneumoniae ds221 but Δjanus::EF-rseP-H18>A | This study |
| ms2 | S. pneumoniae ds221 but Δjanus::EF-rseP-E19>A | This study |
| ms3 | S. pneumoniae ds221 but Δjanus::EF-rseP-H22>A | This study |
| ms4 | S. pneumoniae ds221 but Δjanus::EF-rseP-Y24>A | This study |
| ms5 | S. pneumoniae ds221 but Δjanus::EF-rseP-HExxH>AAxxA | This study |

[a]Cm, chloramphenicol; Ery, erythromycin; Spc, spectinomycin; Kan, kanamycin; Sm, streptomycin.

TABLE 3

MIC 50 values (nM) of LsbB family bacteriocins against different bacterial species.

| Indicator strain | LsbB | EntK1 | Ent-EJ97 |
|---|---|---|---|
| Staphylococcus. aureus LMGT 3310 | >7000 | >5500 | 590 |
| S. aureus LMGT 3260 | >7000 | >5500 | 2300 |
| S. aureus LMGT 3266 | >7000 | >5500 | 1175 |
| S. aureus LMGT 3258 | >7000 | >5500 | >4700 |
| S. aureus LMGT 3289 | >7000 | >5500 | >4700 |
| S. aureus LMGT 3272 | >7000 | >5500 | 1175 |
| S. epidermidis LMGT 3026 | >7000 | >5500 | >4700 |
| Enterococcus. faecalis LMGT 3199 | >7000 | >5500 | 145 |
| E. faecalis LMGT 3571 | >7000 | >5500 | 295 |
| E. faecalis LMGT 3572 | >7000 | >5500 | 145 |
| E. faecalis LMGT 3330 | >7000 | >5500 | 145 |
| E. faecalis LMGT 3143 | >7000 | >5500 | 145 |
| E. faecalis LMGT 3359 | >7000 | >5500 | 145 |
| E. faecalis LMGT 3200 | >7000 | >5500 | 295 |
| E. faecalis LMGT 3386 | >7000 | >5500 | 295 |
| E. faecalis LMGT 3370 | >7000 | 5500 | 145 |
| E. faecalis LMGT 3567 | >7000 | >5500 | 295 |
| E. faecalis LMGT 3358 | >7000 | 2700 | 75 |
| E. faecium LMGT 3599 | >7000 | 85 | 145 |
| E. faecium LMGT 2787 | >7000 | 20 | 145 |
| E. faecium LMGT 3193 | >7000 | 85 | 145 |
| E. faecium LMGT 3110 | >7000 | 45 | 295 |
| E. faecium LMGT 3104 | >7000 | 10 | 145 |
| E. faecium LMGT 3313 | >7000 | 85 | 145 |
| E. faecium LMGT 3192 | >7000 | 20 | 295 |
| E. faecium LMGT 2769 | >7000 | 45 | 145 |
| E. hirae LMGT 3236 | >7000 | 45 | 75 |
| Lactococcus garvieae LMGT 1546 | >7000 | 1370 | 295 |
| L. garvieae LMGT 2217 | >7000 | 340 | 295 |
| L. curvatus LMGT 2355 | >7000 | 5500 | 145 |
| L. lactis IL1403 | 0.5 | 170 | 37 |
| L. lactis LMGT 2233 | >7000 | >5500 | 145 |
| L. lactis LMGT 2084 | >7000 | >5500 | 295 |
| L. lactis LMGT 2095 | >7000 | >5500 | 145 |
| L. cremoris LMGT 2057 | >7000 | >5500 | 145 |
| Lactobacillus sakei LMGT 2334 | >7000 | >5500 | >4700 |
| Bacillus cereus LMGT 2805 | >7000 | >5500 | >4700 |
| B. cereus LMGT 3025 | >7000 | >5500 | 2300 |
| B. cereus LMGT 2731 | >7000 | >5500 | >4700 |
| B. cercus LMGT 2711 | >7000 | 2750 | >4700 |
| B. cercus LMGT 2735 | >7000 | >5500 | >4700 |
| Listeria monocytogenes LMGT 2651 | >7000 | >5500 | 2300 |
| L. monocytogenes LMGT 2605 | >7000 | >5500 | 1175 |

TABLE 4

MIC 50 values (nM) of EntK1 and EntEJ97 against E. faecium strains isolated from blood in patients from different hospitals in Europe.

| E. faecium indicator strain | EntK1 | EntEJ97 |
|---|---|---|
| AH137 | 10 | 75 |
| UW6920 | 45 | 145 |
| P032 inv-4 | 20 | 37 |
| 602589 | 45 | 145 |
| P040 INV-25 | 20 | 75 |
| A11 EFH2/00 | 45 | 75 |
| 130409015079* | 20 | 37 |
| 928379 A* | 20 | 75 |
| PO1402593* | 20 | 75 |
| 14-597963* | 45 | 145 |

*Vancomycin-resistant strains

TABLE 5

Sensitivity of S. pneumonia clones to EntEJ97, EntK1 and LsbB.

| Strain | | MIC (nM)* | | |
|---|---|---|---|---|
| S. pneumoniae | Mutation | EntEJ97 | EntK1 | LsbB |
| ds220 non-induced | WT rseP | >4500 | >5500 | >7000 |
| ds220 induced | WT rseP | 18 | 700 | >7000 |
| ms1 | H18>A | 300 | >5500 | >7000 |
| ms2 | E19>A | 300 | >5500 | >7000 |
| ms3 | H22>A | 300 | >5500 | >7000 |
| ms4 | Y24>A | 18 | 700 | >7000 |
| ms5 | HExxH>AAxxA | 600 | >5500 | >7000 |
| ds 221 | no rseP | >4500 | >5500 | >7000 |

*Bacteriocins were active only when rseP (WT or mutated) was induced with ComS (2 µM). Without ComS the cells were resistant to the bacteriocins. ComS was not toxic to the cells even at 20 µM.

Discussion

Structural analyses by CD spectroscopy showed that EntK1 was unstructured in water but became structured when exposed to membrane-mimicking environments (DPC-micelles or TFE).

The structure of EntK1 in 50% TFE is very similar to that of LsbB (FIG. 1). Both bacteriocins have an N-terminal part mostly composed of an amphiphilic α-helical motif, and an unstructured C-terminal half. EntK1's α-helix is longer than the one of LsbB, being 16-19 residues, versus 13-15 residues in LsbB. A closer look at the α-helices of EntK1 and LsbB showed that both are amphiphilic with the basic amino acids along one side of the helix and nonpolar residues along the other side (data not shown). The α-helical part of the bacteriocins is believed to be involved in a pore-formation mechanism, where the hydrophobic part is facing the hydrophobic core of the membrane or a protein (receptor), while the hydrophilic part is facing the pore to cause cellular leakage. The C-terminal unstructured parts of EntK1 and LsbB are about the same lengths, 10-13 residues and more similar in sequence. Structure prediction servers (PONDR® VL-XT, JPred 4) indicated that EntEJ97 also contains an α-helix from Lys10 to Gly 35 with an unstructured C-terminal tail of 10 residues, which corresponds with our data on LsbB and EntK1 structures.

Besides EntK1 and LsbB, structures of three other leaderless bacteriocins have been obtained so far—Enterocin 7, Lacticin Q and Aureocin A53. Unlike EntK1 and LsbB these bacteriocins are structured in water. Enterocin 7—a two-peptide bacteriocin, where both peptides have a similar fold, consists of N-terminal, middle and C-terminal helices (Lohans et al., 2013, Biochemistry, 52:3987-3994). Lacticin Q and aureocin A53 both consist of 4 helices surrounding a hydrophobic core (Acedo et al., 2016, Biochemistry, 55:733-742). The structures of enterocin 7, lacticin Q and aureocin A53 resemble the structure of circular bacteriocins, which are also highly structured in aqueous solutions. EntK1 and LsbB structures are very different from those bacteriocins by being unstructured in water and containing only one single helix (FIG. 1).

EntEJ97 and EntK1 employ the enterococcal RseP (in addition to the lactococcal one) as receptor. The lactococcal Zn-dependent metallopeptidase RseP has been shown to be responsible for the sensitivity to LsbB in L. lactis IL1403 (Uzelac et al., 2013, J. Bacteriol., 195:5614-5621). According to our study, this conclusion is based on the fact that mutants of E. faecalis LMGT3358/E. faecium LMGT2787 that are highly resistant to EntEJ97/EntK1, contain frameshift mutations in rseP, and, more conclusively, heterologous expression of the enterococcal rseP rendered resistant pneumococcal cells sensitive to these bacteriocins (Table 5). However, at least in the case of *E. faecalis* LMGT3358, EntEJ97 LR mutants had intact rseP. Both types of resistance were specific to EntEJ97 and EntK1 because all resistant cells were sensitive to the non-related bacteriocins BHT-B (leaderless type) and garvicin ML (circular type). Furthermore, both (high and low) types of resistance share one common feature—they emerge at the standard growth temperature of 30° C. but not at the elevated 45° C., indicating that both resistance types are linked to the stress response (FIG. 2).

RseP deletion mutants have shown increased susceptibility to lysozyme and other treatments compared to the susceptibility of the WT strain (Varahan et al., 2103, J Bacteriol., 195:3125-3134) and RseP plays a role in the bacterial stress response (Kim, 2015, J. Microbiol., 53:306-310, Alba et al., 2002, Genes Dev., 16:2156-2168). In our study, enterococcal EntK1 and EntEJ97 resistant mutants with frame shift rseP obtained at 30° C. could not grow at 45° C., while the WT cells grew well. However, in addition, resistance types in which no mutations in resP existed were also susceptible to stress.

The putative active site of enterococcal RseP proteases is located near the N—terminal part of the molecule and contains a consensus sequence motif HExxH, in which the two histidine residues are thought to coordinate a zinc atom together with a conserved glutamate residue. *E. coli* RseP active site is located ~14 Å into the lipid membrane surface (Feng et al., 2007, Science, 318:1608-1612). According to our results, replacing the conserved residues with alanines in *E. faecalis* RseP increased cells resistance to EntEJ97 and EntK1 especially when all three conserved residues were replaced. However, even this version of RseP did not give total resistance to EntEJ97 unlike the HR mutants of *E. faecalis*, meaning that the active site of RseP is only partly and/or indirectly involved in receptor/target recognition by the EntEJ97/EntK1 bacteriocins. Our results strongly suggest that the proteolytic active site of RseP is somehow involved in the receptor function and thereby the bacteriocin activity.

However, multiple sequence alignment analysis (using Clustal Omega) of many RseP (30 from *E. faecalis* and 30 from *E. faecium*) did not show any pronounced differences between the two RseP groups (data not shown). Thus, the properties of RseP that define the different levels of sensitivity toward EntEJ97 and EntK1 await further investigation.

Example 2: Preparation of EntK1 and EntEJ97 Variants and their Effects on Various Bacteria Materials and Methods Bacterial strains, growth conditions, bacteriocins and antimicrobial assays.

All the strains (see below) used in minimal inhibitory concentration (MIC) assays (Ovchinnikov et al., 2017, Front Microbiol., 8, p774, doi:10.3389/fmicb.2017.00774) were grown in BHI medium (Oxoid) at 30° C. without shaking. The tested strains were obtained from the LMG collection. EntK1 (SEQ ID NO:1), EntEJ97 (SEQ ID NO:2), GarKS, EntEJ97short (SEQ ID NO:3), K1-EJ (also known as EntK1J97) hybrid (SEQ ID NO:4) and EJ-K1 (SEQ ID NO:5) hybrid and were synthesized by Pepmic Co., LTD, China with 98-99% purity. NisinZ and micrococcin P1 were purified from source. Synthesized peptides were solubilized to concentrations of 10.0-0.1 mg/ml in 0.1% (vol/vol) trifluoroacetic acid and stored at −20° C. until use.

Garvicin KS is made up of 3 peptides:

```
                                             (SEQ ID NO: 43)
MGAIIKAGAKIVGKGVLGGGASWLGWNVGEKIWK (SEQ ID NO: 44)
MGAIIKAGAKIIGKGLLGGAAGGATYGGLKKIFG;
and (SEQ ID NO: 45)
MGAIIKAGAKIVGKGALTGGGVWLAEKLFGGK
```

NisinZ has the sequence: ITSISLCTPGCKTGALMGCNMKTATCNCSIHVSK (SEQ ID NO:46)

Micrococcin P1 has the structure:

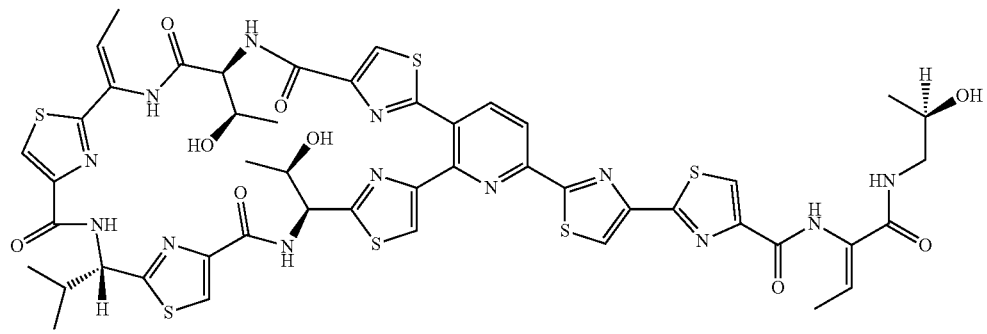

Micrococcin P1

The study of EntK1 and EntEJ97 inhibition spectrum showed an interesting detail—EntK1 had generally narrower antibacterial spectrum than EntEJ97. Against *E. faecium* strains EntK1 was much more potent (i.e., lower MIC values) than EntEJ97 (Table 3, 4). EntEJ97 was equally active against *E. faecalis* and *E. faecium* (Table 3, 4).

Bacteriocin activity was determined using a microtitre plate assay. The plates were incubated at 30° C. for 8 h and the growth was measured spectrophotometrically at 600 nm ($A_{600}$) with 15 min intervals using SPECTROstarNano (BMG LABTECH, Germany). The MIC was defined as the bacteriocin concentration that inhibited the growth of the indicator strain by at least 50% in 200 µl culture (i.e., 50% of the turbidity of the control culture without bacteriocin).

Results

The MIC values that were obtained for EntK1, EntEJ97 and the hybrid peptides against selected pathogenic bacteria isolates are shown in Tables 6A and B. The results show that EntEJ97, EntK1 and their variants EntEJ97short, K1-EJ hybrid and EJ-K1 hybrid are effective against *S. pseudointermedius, S. haemolyticus, E. hirae, E. faecium, E. faecalis*, as well as *S. aureus* and *Listeria*. Particular efficacy was observed against *S. pseudointermedius* (for EntEJ97 short) and *S. haemolyticus* (EntEJ97short and K1-EJ hybrid) compared to other bacteriocins (Table 6B). EntEJ97short was particularly effective against *E. hirae, E. faecalis* and *S. pseudointermedius* and K1-EJ proved particularly effective against *E. hirae, E. faecium, E. faecalis* and *S. haemolyticus*.

TABLE 6

MIC values for EntK1, EntEJ97 and hybrid peptides against selected pathogenic bacteria isolates

A

| Bacteriocin | µg/ml SP 4012 | µg/ml SP 4013 | µg/ml SP 4014 | µg/ml SH 4015 | µg/ml SH 4016 | µg/ml KAVA | µg/ml Sa ATCC 33591 | µg/ml Sa 3328 | µg/ml Sa 3242 | µg/ml Sa3324 | µg/ml Sa3323 |
|---|---|---|---|---|---|---|---|---|---|---|---|
| GarKS | 6.25 | 6.25 | 6.25 | 6.25 | 6.25 | 6.25-12.5 | 12.5 | 3.1 | 3.1 | 6.25 | 6.25 |
| NisinZ | 0.4 | 0.4 | 0.4 | 1.6-3.1 | 1.6-3.1 | 1.6-3.1 | 0.8 | 0.8 | 3.1 | 1.6 | 6.25 |
| EntEJ97 | 12.5 | 12.5 | 12.5 | 12.5 | 12.5 | >50 | >50 | 6.25 | 6.25 | 12.5 | 6.25 |
| EntEJ97short | 3.1 | 3.1 | 1.6-3.1 | 1.6-3.1 | 1.6-3.1 | >50 | >50 | 3.1 | 12.5 | 6.25 | 3.1-6.25 |
| K1-EJ hybrid | 25 | 12.5 | 12.5 | 0.8 | 0.8-1.6 | >50 | >50 | 3.1 | 3.1 | 6.25 | 3.2-6.25 |
| EJ-K1 hybrid | >50 | >50 | >50 | 50 | 50 | >50 | >50 | 6.25 | 12.5 | 12.5 | 3.2-6.25 |
| micrococcinP1 | 0.4 | 0.4 | 0.8 | 1.6 | 1.6 | >12.5 | 0.4 | 0.1 | 0.2 | 0.1 | 0.1 |

B

| Bacteriocin | *E. hirae* (4) | *E. faecium* (2) | *E. faecalis* (2) | *S. pseudointermedius* (3) | *S. aureus* (5) | *Listeria* spp. (3) |
|---|---|---|---|---|---|---|
| EJ97 | 0.4-1.6 | 0.8-1.6 | 3.1 | 12.5 | 6.25->50 | 12.5-25 |
| EJshort | 0.1-0.4 | 12.5-25 | 1.6 | 1.6-31 | 3.1->50 | >50 |
| K1-EJ hybrid | 0.1-0.4 | <0.05-0.4 | 1.6-3.1 | 12.5-25 | 3.1->50 | 6.25-25 |
| EJ-K1 hybrid | 3.2-6.3 | 3.15 | 25-50 | 50 | 6.25->50 | 12.5->50 |
| K1 | 0.2-0.8 | <0.02-0.4 | >25 | ND | >25 | >50 |

SP = *S. pseudointermedius*;
SH = *S. haemolyticus*;
KAVA = micrococcin P1 (used as control);
Sa = *S. aureus*
ND: Not determined

The invention claimed is:

1. A bacteriocin peptide of less than 50 amino acids comprising an amino acid sequence selected from:
   a) MKFKFNPTGTIVKKLTQYEINWYKQQYGRYPW-ERPVA (SEQ ID NO: 4); and
   b) a sequence with at least 85% sequence identity to sequence a), wherein sequence b) comprises at least the consensus sequence KXXXGXXPWE (SEQ ID NO: 40).

2. The bacteriocin peptide of claim 1, consisting of an amino acid sequence selected from:
   a) MKFKFNPTGTIVKKLTQYEINWYKQQYGRYPW-ERPVA (SEQ ID NO: 4); and
   b) a sequence with at least 85% sequence identity to sequence a), wherein sequence b) comprises at least the consensus sequence KXXXGXXPWE (SEQ ID NO: 40).

3. A method of killing, damaging or preventing the replication of bacteria comprising administering or applying the bacteriocin of claim 1 to said bacteria.

4. The method of claim 3 wherein said bacteria is *E. faecium, E. faecalis, E. hirae, S. pseudointermedius* and/or *S. hemolyticus*.

5. The method of claim 3 wherein said bacteria is *E. faecium, E. faecalis* and/or *S. hemolyticus*.

6. The method of claim 4, wherein said method is performed in vitro.

7. The method of claim 4, wherein the method is for disinfecting or decontaminating an item, of bacteria present on said item, wherein the method comprises covering, impregnating, or coating said item with said bacteriocin or applying said bacteriocin to said item, wherein optionally in said method said bacteria are subjected to heating at between 40 and 50° C. before, during and/or after administering or applying said bacteriocin.

8. The method of claim 7, wherein said item is
   i) a medical device, instrument, implement or equipment, a prosthetic, an implant, a scaffold, or a tissue or wound dressing, or
   ii) a personal health care product.

9. The method of claim 8, wherein said personal health care product is toothpaste, mouthwash, skin cream, lotion or spray.

10. A method of treating or preventing a bacterial infection in a subject or patient comprising administering the bacteriocin of claim 1 to said subject or patient or to a part of said subject's or patient's body.

11. The method of claim 10, wherein said subject or patient is a mammal.

12. The method of claim 10, wherein said bacterial infection is an infection on the skin and said bacteriocin is administered topically.

13. The method of claim 12, wherein said bacterial infection is caused by *E. faecium, E. faecalis* and/or *S. hemolyticus*.

14. The method of claim 10, wherein said bacteriocin is provided in a host cell which produces said bacteriocin.

15. The method of claim 10, wherein said bacteriocin is co-administered or co-applied with one or more additional antibacterial agents, wherein optionally said bacteriocin is in the form of a composition comprising said bacteriocin and said one more additional antibacterial agents.

16. The method of claim 15, wherein said one or more additional antibacterial agents are selected from one or more bacteriocins or antibiotics.

* * * * *